(12) United States Patent
Olesberg et al.

(10) Patent No.: US 9,540,701 B2
(45) Date of Patent: *Jan. 10, 2017

(54) APPARATUS AND METHOD FOR AUTOMATED PROCESS MONITORING AND CONTROL WITH NEAR INFRARED SPECTROSCOPY

(71) Applicant: ASL Analytical, Inc., Coralville, IA (US)

(72) Inventors: Jonathon Todd Olesberg, Iowa City, IA (US); Mark Allen Arnold, Iowa City, IA (US); Gary Wray Small, Coralville, IA (US); Edwin John Koerperick, North Liberty, IA (US); Christine Esther Evans, North Liberty, IA (US)

(73) Assignee: ASL ANALYTICAL, INC., Coralville, IA (US)

( * ) Notice: Subject to any disclaimer, the term of this patent is extended or adjusted under 35 U.S.C. 154(b) by 114 days.

This patent is subject to a terminal disclaimer.

(21) Appl. No.: 14/631,917

(22) Filed: Feb. 26, 2015

(65) Prior Publication Data

US 2015/0247794 A1 Sep. 3, 2015

Related U.S. Application Data

(60) Provisional application No. 61/946,170, filed on Feb. 28, 2014, provisional application No. 61/988,700, (Continued)

(51) Int. Cl.
*C12Q 3/00* (2006.01)
*G01N 21/359* (2014.01)
(Continued)

(52) U.S. Cl.
CPC ............... *C12Q 3/00* (2013.01); *G01N 21/314* (2013.01); *G01N 21/359* (2013.01);
(Continued)

(58) Field of Classification Search
CPC G01N 21/314; G01N 21/3577; G01N 21/359; G01N 21/39
See application file for complete search history.

(56) References Cited

U.S. PATENT DOCUMENTS

| 5,023,804 A | 6/1991 | Hoult | |
| 5,223,715 A * | 6/1993 | Taylor | G01N 21/255 250/339.02 |

(Continued)

*Primary Examiner* — Christine Sung

(57) ABSTRACT

A system and method for continuous, real-time process monitoring and control by means of near-infrared (NIR) spectroscopy provides analysis of static or flowing fluid streams which may range from clear to highly optically dense, including fluids primarily of aqueous composition. A NIR source passes through a wavelength selector to select one or more spectral segments, which are passed through the fluid stream at a fluid sampling interface and received at a sensor. A wavelength reference material is positioned in the optical path for calibration. Quantification of a plurality of characteristics or parameters of a fluid and suspended solids or cells contained therein may be performed. An all-solid-state implementation of the optical system ensures high robustness in laboratory and industrial settings.

50 Claims, 11 Drawing Sheets

Related U.S. Application Data filed on May 5, 2014, provisional application No. 61/953,374, filed on Mar. 14, 2014.

(51) Int. Cl.
| | | |
|---|---|---|
| *G01N 21/39* | (2006.01) | |
| *G01N 21/3577* | (2014.01) | |
| *G01N 21/31* | (2006.01) | |
| *G01N 21/51* | (2006.01) | |
| *G01N 21/64* | (2006.01) | |
| *G01N 21/65* | (2006.01) | |

(52) U.S. Cl.
CPC ......... *G01N 21/3577* (2013.01); *G01N 21/39* (2013.01); *G01N 21/51* (2013.01); *G01N 21/645* (2013.01); *G01N 21/65* (2013.01); *G01N 2021/399* (2013.01); *G01N 2201/067* (2013.01); *G01N 2201/0846* (2013.01)

(56) References Cited

U.S. PATENT DOCUMENTS

| | | |
|---|---|---|
| 5,933,792 A | 8/1999 | Andersen et al. |
| 5,936,727 A | 8/1999 | Trygstad |
| 6,137,108 A | 10/2000 | DeThomas et al. |
| 6,297,505 B1 | 10/2001 | Frandsen et al. |
| 6,395,538 B1 | 5/2002 | Naughton et al. |
| 6,483,583 B1 | 11/2002 | Wright et al. |
| 7,057,164 B2 | 6/2006 | Springsteen et al. |
| 7,087,901 B2 | 8/2006 | Ambuel |
| 7,288,767 B2 | 10/2007 | Ridder |
| 7,379,783 B2 | 5/2008 | Popp |
| 7,379,784 B2 | 5/2008 | Popp |
| 7,392,107 B2 | 6/2008 | Popp |
| 7,799,273 B2 | 9/2010 | Popp |
| 7,839,502 B2 | 11/2010 | Lukas et al. |
| 8,078,322 B2 | 12/2011 | Grieb et al. |
| 8,491,839 B2 | 7/2013 | Popp |
| 8,545,759 B2 | 10/2013 | Niazi |
| 8,591,811 B2 | 11/2013 | Popp |
| 8,660,680 B2 | 2/2014 | Popp |
| 8,873,047 B2 * | 10/2014 | Wang ............... G02B 27/1006 356/326 |
| 9,008,815 B2 | 4/2015 | Popp |
| 9,092,028 B2 | 7/2015 | Popp |
| 9,195,228 B2 | 11/2015 | Popp |
| 2005/0240090 A1 * | 10/2005 | Ruchti ............. A61B 5/14532 600/316 |
| 2008/0290279 A1 * | 11/2008 | Juhl ..................... G01J 3/28 250/339.08 |
| 2009/0104594 A1 | 4/2009 | Webb |
| 2009/0312851 A1 | 12/2009 | Mishra |
| 2011/0081672 A1 | 4/2011 | Andersen et al. |
| 2013/0228690 A1 | 9/2013 | Juhl |
| 2013/0286380 A1 | 10/2013 | Selker et al. |

* cited by examiner

APPARATUS AND METHOD FOR AUTOMATED PROCESS MONITORING AND CONTROL WITH NEAR INFRARED SPECTROSCOPY

CROSS-REFERENCE TO RELATED APPLICATIONS

This application claims the benefit of U.S. provisional patent application No. 61/946,170, filed Feb. 28, 2014, for "Near Infrared Process Monitoring and Control"; U.S. provisional patent application No. 61/988,700, filed May 5, 2014, for "System for Near-Infrared Process Monitoring and Control"; and U.S. provisional patent application No. 61/953,374, filed Mar. 14, 2014, for "Optical Flow Cell with Disposable Fluid Flow Cartridge." Such applications are incorporated herein by reference in their entirety.

STATEMENT REGARDING FEDERALLY SPONSORED RESEARCH OR DEVELOPMENT

This invention was made with government support under grant nos. 912828 and 1058434 awarded by the National Science Foundation. The government has certain rights in the invention.

BACKGROUND

The present invention relates to a system for making continuous, real-time, non-destructive measurements of constituents in optically dense fluids for applications including, but not limited to, pharmaceutical, food, beverage, fuel, enzyme, and chemical manufacturing as well as other industrial processes. In particular, the present invention is well-suited for performing measurements in aqueous fluids, which is significant in a plurality of applications such as bioprocessing.

Access to continuous real-time data on conditions and constituents in fluid processing applications is highly desirable in a multitude of branches of industry and research. While robust sensors are widely available to measure parameters such as pH, dissolved oxygen (DO), temperature, pressure, etc. in-situ and in real-time, such sensors to measure quantities of chemical constituents and suspended solids in fluids in real-time and in a robust manner have remained elusive in the art. Furthermore, sensors that are capable of measuring constituent concentrations often do so in a destructive manner, have inadequate sampling frequencies, and often require manual sampling and off-line analysis.

Quantification of constituent concentrations during fluid processes is most commonly performed by manual sampling and off-line analysis. Techniques such as high performance liquid chromatography (HPLC), gas chromatography-mass spectroscopy (GCMS), as well as various enzyme- and reagent-based electrochemical approaches are available for off-line constituent quantification. Such techniques may be accurate, but suffer in that they are destructive to the sample, often require expensive consumables, take long times to complete, and are prone to calibration difficulties. In addition, the hardware required to perform these analyses is commonly expensive to maintain and typically demand highly trained and dedicated personnel. Due to the labor requirements of manual sampling and time required to perform a measurement, the sampling frequency is typically insufficient to enable any meaningful feedback control of a process. In order to reduce the labor cost of manual sample analysis, samples are commonly run in batches and after a process has run to completion. In this case, constituent quantification data are of limited value as control strategies cannot be implemented and corrective action cannot be taken during a process.

Sampling systems are available to automate the sampling process with some of these measurement approaches, and feedback control capabilities have been advertised. However, the aforementioned limitations still apply, and the total sample and priming volume are often on the order of 1-10 mL, making these systems inapplicable to miniature- and micro-sized fluid processing vessels which are increasing in popularity in research and development environments.

Measurement of characteristics of fluids by optical means is well-known in the art. Electromagnetic radiation impinging on a medium may interact with the medium by absorption, scattering, or fluorescence. Measurement of transmitted, reflected, scattered, or fluoresced radiation by an appropriate sensor may be used to determine multiple characteristics or properties of the medium, such as concentrations of constituents or turbidity, simultaneously. Typical techniques include visible spectroscopy, infrared spectroscopy, and optical scattering measurements such as Raman spectroscopy. On-line constituent monitors utilizing Raman spectroscopy have been described in the prior art and scientific literature, however commercial examples of such systems are most commonly sold as generalized measurement platforms requiring a highly skilled operator to produce useful output. Fundamental issues such as fluorescence background and weak signal often limit the performance of Raman analyzers—while the Raman signal increases with the fourth power of the excitation laser frequency, background fluorescence increases proportionally with the laser frequency. Use of longer wavelength laser sources reduces the background fluorescence, however higher powers must often be applied to the sample to produce acceptable signal levels, and sample damage may result.

Analytical instruments utilizing the near-infrared (NIR) spectral range (roughly 700 to 3000 nm) have found application in numerous industrial and laboratory applications such as chemical processing, food and beverage manufacturing, petroleum processing, and pharmaceutical manufacturing. A variety of configurations of NIR spectrometers and analyzers have been demonstrated in the prior art, having the intended function of determining one or more characteristics or parameters of a substance or its constituents. All such instruments execute similar fundamental operations: generate NIR radiation; direct said radiation to a sample; resolve the resultant radiation having interacted with the sample spectrally; measure the resolved radiation with an appropriate sensor; predict or measure characteristics of the sample or its constituents. These operations need not be performed in the specified order here. For example, a tunable light source may be employed rather than spectrally resolving broad-band radiation into multiple smaller bands. Separation of the radiation into discrete bands may also be performed before interaction with the sample takes place.

Various methods may be employed to perform the fundamental spectroscopic operations. Light sources may include light emitting diodes (LEDs), tungsten halogen lamps, micro electromechanical systems (MEMS)-based sources, and infrared lasers. Spectral resolution of the optical energy may be performed by grating-based solutions (scanning or fixed); Fourier transform infrared (FTIR) interferometry; interference filtering; and acousto-optical tunable filters (AOTF). The sample may be interrogated by means of optical transmission, transflection, reflection, scattering, or fluorescence. The sample may be flowing or static. A variety of sample interrogation methods exist. Furthermore, both free-space and fiber-coupled optical delivery and collection means are possible. Detection of NIR radiation may be accomplished by means of single element or array sensors. Semiconductor sensors comprising, for example: silicon; germanium; indium arsenide (InAs); indium gallium arsenide (InGaAs); indium antimonide (InSb); and lead sulfide (PbS) are available. Other detection platforms including photomultiplier tubes (PMT) and thermal sensors are also available. Determination of sample characteristics, parameters, and constituent concentrations may be performed by one or more chemometric approaches.

In most implementations in the prior art, resolution of broad-band NIR radiation is performed by grating- and FTIR-based approaches. While these approaches may offer advantages in throughput and/or resolution, they are often insufficiently robust for deployment in industrial or manufacturing settings. For example, thermal and mechanical disturbances in industrial environments combined with the inherent mechanical sensitivity of these spectroscopic approaches often limits practical relevance in industry. Furthermore, FTIR instrumentation is often bulky and not accommodating to miniaturization, making such platforms difficult to deploy in laboratory and industrial environments where space is at a premium. Another common limitation of prior art NIR instrumentation when applied to fluid analysis is the speed over which such instruments scan over the wavelength range of interest. Such instruments commonly provide scan times ranging from several hundred milliseconds to several seconds. In applications with flowing or agitated fluid, gas bubbles and solids suspended within the fluid often traverse the optical beam used to interrogate the fluid. If the transit time of such bubbles or suspended solids is faster than the scan time, detection of such disturbances and minimization of the effects they impart on a measurement becomes difficult or impossible.

Optical emitters, elements, and in particular sensors utilized in prior art NIR analyzers are often optimized for spectroscopy in the first C—H overtone region. This also roughly overlaps with the optical telecommunications wavelengths in the 1.3 to 1.6 μm spectral band. Optics and optical emitters in this spectral region are well-developed and widely available due to ubiquitous use in the telecommunications industry. Systems optimized for spectroscopy in the combination band of 1.6 to 2.6 μm are less common. This wavelength band is of particular relevance for measurements of constituent measurements in aqueous fluids due to strong optical absorption features of the constituents as well as the favorable optical transmission of water. Liquid water presents strong optical absorption bands in the infrared due to fundamental O—H stretching vibrations. While strong absorption peaks exist near 3450 $cm^{-1}$ (2.9 μm) and 5128 $cm^{-1}$ (1.95 μm), the combination region therebetween is sufficiently optically transparent to enable transmission measurements to be performed in aqueous solutions.

Sampling approaches in common NIR analyzers include external and internal flow cells, cuvettes, vials, and fiber optically coupled probes. Performance from external flow cells and fiber optic probes tends to suffer due to significant NIR absorption in common optical fibers as well as low throughput owing to the large emitting area of NIR optical emitters compared to optical fiber apertures. Sampling approaches internal to the instrument often present connection and sample loop sterility challenges. Permanent hardware implementations of flow cells are common, though not particularly amenable to the cleaning and sterilization requirements of biotechnology industries.

Another significant limitation of prior art NIR analyzers is that they are most commonly developed as generalized spectroscopic instruments intended for use in a wide variety of applications. While the apparent flexibility may appeal to some users, these platforms often require a highly skilled operator to generate useful output from the instrument and data analysis software.

To overcome the limitations of prior art NIR analyzers, a platform is desired which: is robust to the environment in industrial facilities; is compact and easily portable; interrogates samples non-destructively, continuously, and in real-time; determines fluid component concentrations continuously within complex, dynamic matrices; accommodates samples that are highly turbid; provides a sterilizable sampling interface that may be disposable; enables process control; remains within specified operating parameters for extended periods of time; has a low maintenance burden; is able to reject spectra contaminated by gas bubbles within the fluid; is able to robustly eliminate outlier spectra due to short-term instrument drift or sporadic events within the process fluid; is readily calibrated for complex and/or dynamic sample conditions; maintains calibration over an extended time period; and does not require a highly skilled operator. Preferably systems may be provided which address as many of the aforementioned limitations as possible.

BRIEF SUMMARY

The present invention provides near infrared spectroscopic instrumentation to continuously and non-destructively quantify levels of constituents and suspended materials in fluids that are either static or flowing and may be of aqueous composition. In various implementations, fluids may range from non-turbid to highly-turbid, and no filtration or processing of the fluid may be required. Electromagnetic radiation in the near-infrared wavelength band is generated, spectrally resolved, delivered to one or more samples which are either static or flowing, measured by one or more appropriate sensors, and analyzed to provide user output and/or control signals. The aforementioned steps need not be performed in the specified order, and may be performed with a plurality of component configurations. Various implementations of the invention find application, for example, in bioprocessing, pharmaceutical research and production, food and beverage manufacturing, agricultural trade and science, chemical processing, and petroleum processing. Certain implementations may also find application in laboratory optical spectroscopic analysis.

An advantage of certain implementations of the present invention over the prior art is that a wavelength reference means comprising a polymer optical element is provided to automatically establish a wavelength axis during operation of the invention. The wavelength reference operation may be executed intermittently or continuously, depending on the particular embodiment of the invention. Use of a polymer optical element as a wavelength reference provides the ability to verify the wavelength axis over a plurality of wavelengths in contrast to prior art implementations that commonly provide wavelength calibration only at a single wavelength or over a generally narrow range of wavelengths. For example, prior art wavelength reference implementations commonly comprise a laser, narrow bandpass filter, notch optical filter, absorptive medium embedded in a substrate, or other chemical means to establish the wavelength at a single point or narrow band of wavelengths.

Embodiments of the present invention perform wavelength axis determination over the entire spectral region of interest, whereby the wavelength axis may be both shifted and scaled. The provision of a wavelength reference utilizing a polymer optical element also allows for mitigation of measurement drift due to, for example, changes in environmental conditions or component performance.

Another advantage of certain implementations of the present invention is that automatic detection of gas bubbles in the fluid sample and rejection of data points with excessive contamination by entrapped bubbles greatly enhances system performance over prior art. Attenuation of near-infrared light by water provides the means to sense changes in the length of optical path through a solution, thereby providing a quantification of measurement contamination by gas bubbles present within the fluid sample.

Due to the use of near infrared light in the measurement of fluid samples, certain implementations of the present invention are able to perform measurements in a wide range of fluids. Fluid samples may be clear or highly turbid, and do not require filtration or other treatment prior to measurement. Owing to the facts that fluid samples need not be treated, the near-infrared radiation is non-ionizing, and the materials contacting the fluid sample are able to be sterilized, certain implementations provide a measurement whereby the sample is not destroyed or altered. Implementations are provided whereby fluid samples are drawn from a process and subsequently returned to the process after measurement by the present invention, as well as implementations where optical sampling is performed in-situ. Embodiments are also provided whereby fluid samples may be drawn from a process and subsequently discarded. In certain embodiments, measurements may be performed automatically, continuously, in real-time, and in the absence of an operator. Furthermore, certain embodiments of the present invention provide for feedback control of processes whereby one or more quantities of a substance in a process may be measured, and the measurement values used to automatically control desired values of the substance(s) in the process vessel. Process automation by means of feedback control further reduces the labor requirements of monitoring and controlling processes, reduces the probability of human error, and provides for enhanced error detection and outlier condition notification.

Another advantage of certain implementations of the present invention over the prior art is that all spectroscopic analysis is performed within provided software, and operators need not have knowledge of spectroscopy, chemical analysis, or chemometrics. The invention may be calibrated for numerous chemical constituents within various processes; however no specific technical knowledge regarding quantification of the constituents is required of the operator. As these implementations of the present invention utilize near-infrared light, chemical constituents having one or more of, for example, C—H, O—H, C—O, N—H, S—H, and P—H chemical bonds may commonly be measured. Amounts of a variety of alcohols, sugars, lipids, organic acids, fatty acids, peptides, DNA, and proteins within fluid samples may therefore be optically quantified with various embodiments of the present invention. Certain implementations of the present invention also provide for quantification of materials suspended within fluid samples such as particulate matter and cells. Certain implementations are capable of performing measurements in highly complex fluids that may comprise a plurality of substances in addition to the substances targeted for measurement. Measurement results of the quantities of the desired substances are presented simultaneously and continuously to the operator on an output device as well as stored for subsequent use, quality control, and documentation. Minimal attention is required from operators, and thus various implementations of the present invention may operate for extended periods of time without requiring maintenance.

The detailed description and drawings provided herein will offer additional scope to certain implementations of the present invention. It should be understood that the described implementations are provided as examples only. Those skilled in the art will recognize that numerous variations and modifications of the described implementations are within the scope of the invention.

DETAILED DESCRIPTION

As used herein, the terms "optical" and "light" refer to electromagnetic radiation having vacuum wavelengths between 300-20,000 nm.

As used herein, "cartridge" means a housing, case, cover, enclosure or frame generally used to contain and support one or more sections of tubing.

As used herein, "near infrared", "near-infrared", and "NIR" mean the region of the electromagnetic spectrum generally spanning wavenumbers between 3300 $cm^{-1}$ and 14,000 $cm^{-1}$ (corresponding to wavelengths of approximately 0.7 μm to 3.0 μm).

As used herein, "interrogation" and "sampling" mean illuminating a sample with optical radiation and collecting at least a portion of the radiation having interacted with said sample for optical analysis.

As used herein, "constituent" means a chemical analyte, protein, DNA, component in a fluid, cell, or solid suspended in a fluid.

Figure 1:
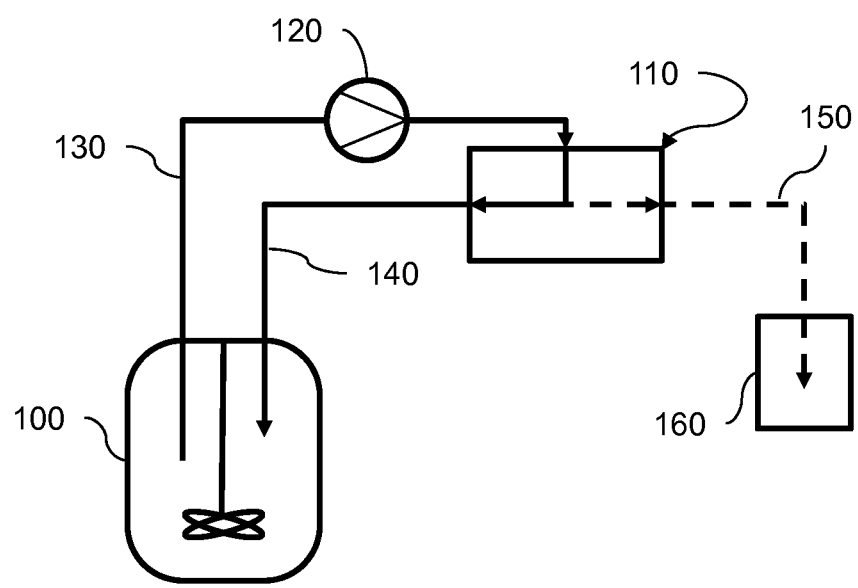
FIG. 1 is a block diagram of an embodiment of the invention connected to a process vessel.

A typical fluid sampling configuration in one embodiment of the present invention is a circulation loop arrangement, as shown in the block diagram in FIG. 1. In this configuration, the optical instrument 110 continuously or intermittently optically interrogates a fluid sample drawn from a process and provides quantified values of one or more substances within the fluid sample on a graphical display 300 shown in FIG. 2. The vessel 100 from which the fluid sample is drawn connects to the optical instrument 110 by means of a pump 120, fluid delivery tubing assembly 130, and fluid return tubing assembly 140. Sampled fluid may also be discarded by means of an exhaust line 150 and waste container 160. This implementation performs spectroscopic measurements on un-filtered process fluid which may be of high turbidity—no treatment of the fluid sample is required, though filtered fluids may also be analyzed. The vessel 100 from which fluid is sampled may comprise a plurality of containers such as chemical reactors, bioreactors, filtration systems, pipes, flasks, and flexible polymer containers depending on the application. Fluid may be sampled from a vessel 100 by a variety of means such as a flexible or metal tube, though numerous alternatives exist. In many fluid processes it is common to provide agitation to the fluid to ensure thorough mixing of the substances contained or suspended in the fluid. Gasses, for example carbon dioxide, oxygen, and air, are also commonly introduced into fluids as part of a process, or are generated as a result of the process as with carbon dioxide production during yeast fermentation. It is commonly desirable to position hardware for fluid sampling such that bubbles of gasses that are introduced into the process or generated by the process are excluded from the fluid sample to be optically interrogated. Gas bubbles are a common source of variation and measurement error in optical and other fluid analysis approaches, and should therefore be excluded to the extent possible.

Figure 2:
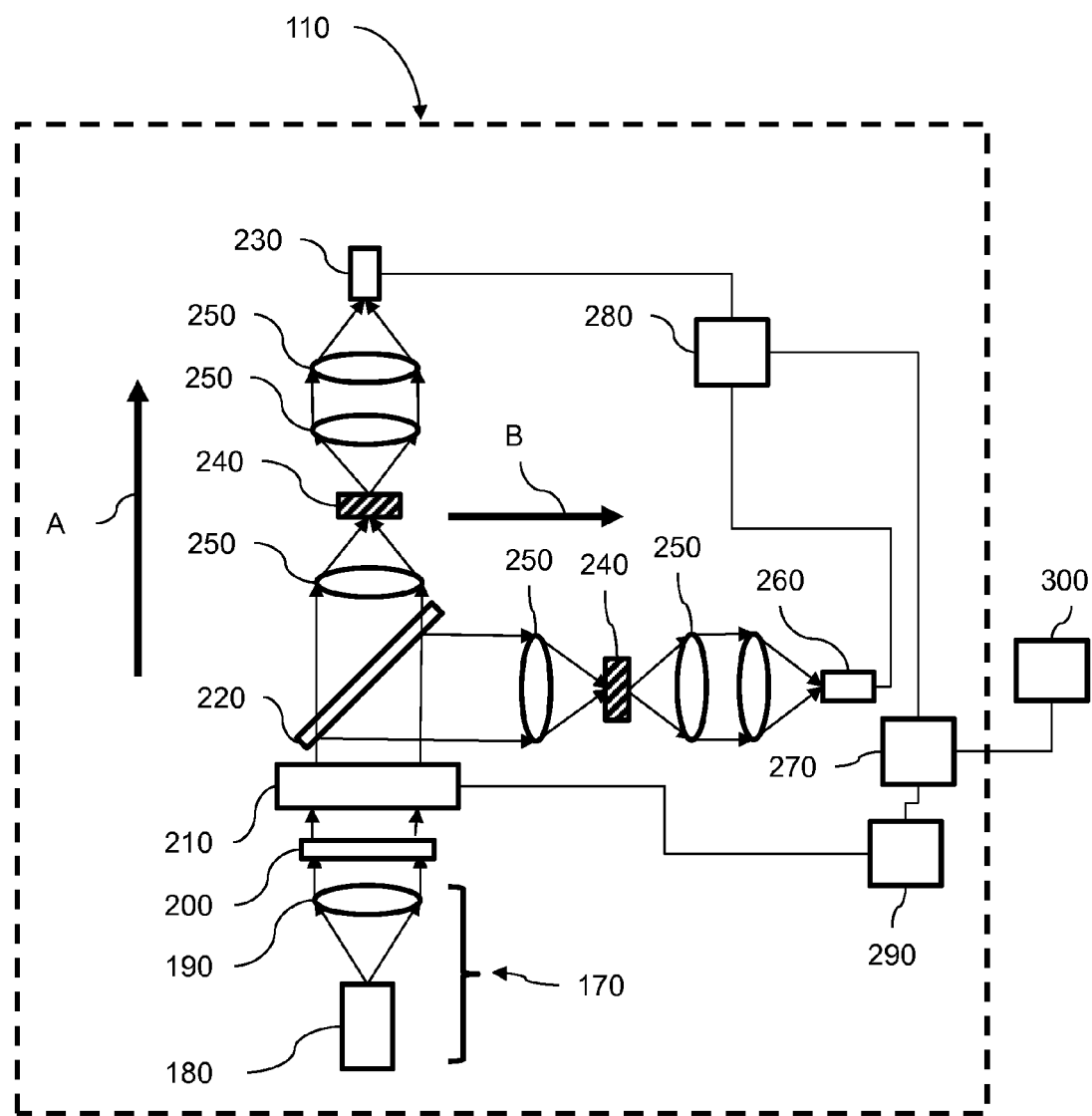
FIG. 2 is a block diagram showing various components of the invention.

A block diagram of an embodiment of the optical instrument 110 is shown in FIG. 2. The instrument 110 comprises an optical emitter 170 configured to emit near-infrared radiation. The optical emitter 170 comprises at least an emitter of near-infrared radiation 180, and may also comprise optical elements such as a lens 190 for collimating or otherwise spatially or spectrally manipulating said near-infrared radiation. In one embodiment, the emitter 180 comprises a broadband optical emitter such as a tungsten halogen bulb. The emitter 180 may also comprise a semiconductor optical emitter such as a light emitting diode (LED), a tunable laser diode (TLD), or a superluminescent diode (SLD). While lamp-based light sources offer low cost and simplicity, they are not generally accommodating to applications such as fiber optic coupling as the filament area is typically much larger than the core diameter of common optical fibers, resulting in substantial optical losses. Semiconductor light sources, on the other hand, may be manufactured with very small emitting areas, and thus coupling to optical fibers can generally be performed with low optical losses.

In an implementation of the present invention, a wavelength reference 200 is provided for calibration of the wavelength axis of the near-infrared optical measurement. In one embodiment, the wavelength reference 200 comprises at least a polymer optical element, and optionally an actuation means to intermittently position the polymer element into an optical beam path. The wavelength reference 200 may also be continuously positioned within a beam path. The polymer optical element should be chosen such that the absorption characteristic of the material has variation within the wavelength range of interest such that a spectrum acquired with the optical instrument 110 may be compared with a previously acquired spectrum to determine the degree to which the two spectra differ. The differences between the spectrum acquired with the optical instrument 110 and a known reference spectrum may be used to confirm or adjust the wavelength axis of a near-infrared measurement. Establishment and verification of the wavelength axis of the measurement provides measurement stability, and maintains an accurate wavelength axis during changing environmental conditions and system component performance. Materials with multiple absorption features within the wavelength range of interest are preferable, with, for example polycarbonate, nylon, Kapton®, polymethylpentene, and polyether ether ketone (PEEK), being candidates for polymer reference materials in the near-infrared. The wavelength reference 200 need not be placed at the specific location in the beam path as shown in FIG. 2.

In the present invention, the wavelength reference operation is preferably performed over the entire wavelength range over which fluid constituent quantification is performed. A regression operation is performed over the wavelength range of interest in order to compare the transmission optical spectrum of the polymer optical element that is acquired with the optical instrument to a previously acquired transmission optical spectrum obtained with a reference instrument. Polymer optical elements are preferably used that exhibit a plurality of optical absorption features over the wavelength range of interest in order to facilitate a high quality regression operation. From the comparison operation, spectral shift and scaling factors may be determined and applied to spectra subsequently acquired with the optical instrument such that the wavelength axis of the optical instrument is stable and well-defined. Such a wavelength reference operation provided by embodiments of the present invention whereby spectral shifting and scaling are performed is preferable to prior art wavelength reference operations. Prior art wavelength reference operations where simple spectral shifting is commonly provided are typically based upon peak fitting to one or few spectral features, and therefore may not provide accurate scaling of the wavelength axis and may be valid only over a limited wavelength range. Embodiments of the present invention provide for performing a plurality of wavelength reference operations throughout a fluid process. For example, a wavelength reference operation may be performed every 30 minutes during fluid processing wherein the fluid process lasts for a period of time of one week or more.

In one embodiment, spectral separation of near-infrared light into one or more segments is performed by a wavelength selector 210 in the optical beam path. Spectral separation of the light from an optical emitter may be performed by means of an acousto-optic tunable filter (AOTF) crystal. This all-solid-state approach of spectral selection has no moving parts, and allows rapid scanning across all wavelengths of interest. Scans of the entire wavelength range of interest may be performed in less than 100 ms, enabling substantial scan averaging to be performed within a standard data collection period, which for typical applications is generally one second to 10 minutes. The rapid scan time over the wavelength range of interest, commonly 100 ms or less per scan, provided by embodiments of the present invention permits robust operation in fluid processes. As the scan time of such embodiments is commonly of a similar time duration to the fluid transit time across the optical beam, scans that are contaminated by gas bubbles or solids may be excluded from further analysis or averaging, or display to a user. In other embodiments of the present invention, the wavelength selector 210 may comprise a planar reflection diffraction grating, a non-planar reflection diffraction grating, or a transmission diffraction grating. Embodiments of the present invention comprising a semiconductor light source in the optical emitter 170 may provide the wavelength selector 210 integrated into the optical emitter 170 such that the light source is tunable. A light source 170 comprising a tunable laser diode would be one such example where the wavelength selector may be integrated with the optical emitter 170. In embodiments of the present invention where the sample in which an optical measurement is performed is a fluid, the spectral resolution of the optical wavelength selector 210 need not be as high as provided by many spectroscopic instruments known in the art. For example, a resolution that may be poorer than 8 $cm^{-1}$ is acceptable in implementations of the present invention as most spectral features in fluid samples are substantially broader than 8 $cm^{-1}$. Instruments such as Fourier transform infrared (FTIR) spectrometers, for example, may provide very high resolutions such as 0.5 $cm^{-1}$. While high spectral resolution may be attractive for gas spectroscopy and other applications, unnecessarily high spectral resolution in spectroscopy of fluid samples may be undesirable as the information gained may be minimal or absent, and the superfluous data merely consume electronic storage space.

In FIG. 2, light in a first optical path travels generally in the direction indicated by arrowed line A. The present invention includes an embodiment where only one optical path is required, said optical path originates at the optical emitter 170, and terminates with a sensor 230 connected to a controller 270 via an analog-to-digital converter 280. Said first optical path further comprises the wavelength selector 210 which is optionally included in the optical emitter 170, the wavelength reference 200, and a fluid sampling means 240. The first optical path may further comprise additional optical components such as lenses 250 for manipulation of the near-infrared light into and out of the fluid sampling means 240. Said additional optical elements may comprise a plurality of optical elements such as flat mirrors, curved mirrors, polarizers, optical filters, waveguides, fibers, wave plates, and beam splitters. In one embodiment, a second optical path, indicated by arrowed line B in FIG. 2, comprises a beam splitter 220 generally intersecting the first optical path, and at least a second sensor 260 connected to a controller 270 via an analog-to-digital converter 280. Said second optical path may further comprise optical elements such as lenses 250 to manipulate light in the second optical path. The sensors 230 and 260 comprise a material optically sensitive to near-infrared light such as indium gallium arsenide (InGaAs), indium antimonide (InSb), indium arsenide (InAs), lead sulfide (PbS), lead selenide (PbSe), and mercury cadmium telluiride (HgCdTe). Sensors 230 and 260 may further comprise coolers such as thermoelectric modules and temperature controllers to improve performance or stability. Sensors may be provided as single-element or multi-element units. Multi-elements sensors such as array sensors may enable increased measurement speed for example when implemented in a spectrograph configuration whereby a grating and multi-element sensor are used in conjunction to enable measurements to be made at multiple wavelengths simultaneously. Said second optical path may be employed for a blank or reference signal where in one embodiment no fluid sample is present in the path. Such a signal is useful for increasing measurement stability, as measurement errors and noise due to fluctuations in the intensity or spectral content of light emerging from the optical emitter 170 may be minimized. Similarly, measurement errors or noise due to environmental conditions, performance variation in the wavelength selector 210, or other conditions common to the first and second optical paths may be reduced. The second optical path may optionally comprise a fluid sampling means 240 as in the first optical path, providing a means for analysis of a second fluid sample. Said second fluid sample may be similar or dissimilar to the fluid sample measured in the first optical path. Such a configuration may be utilized to perform a differential measurement in order to, for instance, reduce the impact of certain fluid constituents on the measurement. As an example, a solution of growth media for a fermentation or cell culture may be introduced as the second fluid sample, thereby reducing the impact of spectral signatures associated with components of said media and increasing measurement accuracy by allowing subtraction of said spectral signatures. Additional optical paths are within the scope of the invention, and said additional optical paths may be utilized for analysis of additional fluid samples, provision of reference signals, wavelength axis reference measurements, or other operations.

Figure 3:
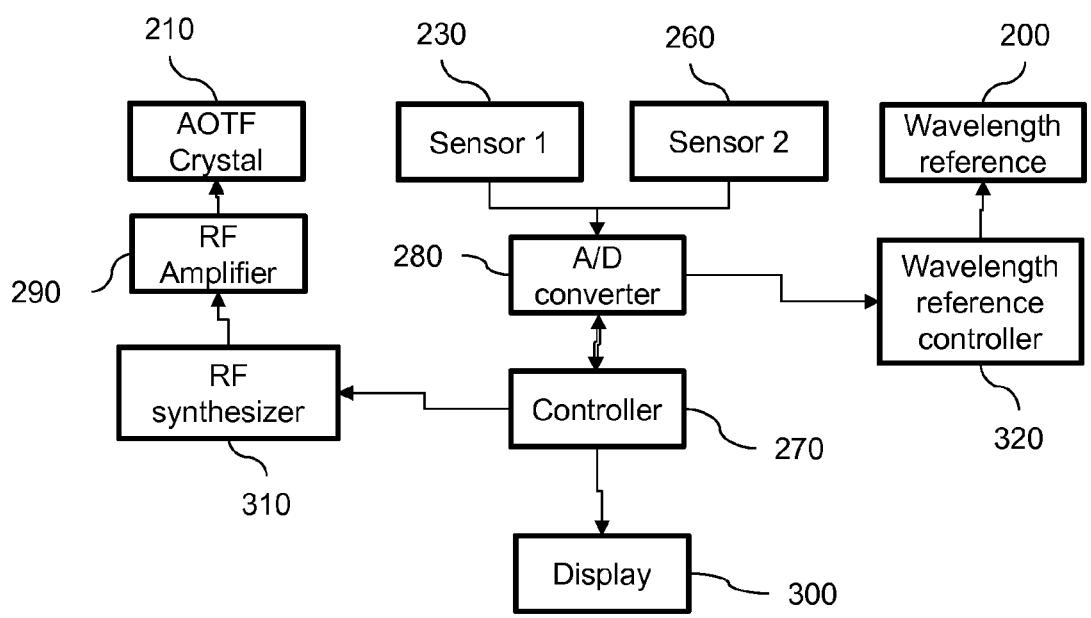
FIG. 3 is a block diagram of the electronic components of the invention.

A block diagram of the major electronic components of an embodiment of the invention comprising an AOTF crystal for the wavelength selector 210, two sensors 230 and 260, and a wavelength reference 200 configured with an actuator is shown in FIG. 3. A controller 270 such as a computer or other microprocessor is provided to accept input from sensors such as 230 and 260, and deliver output signals to control for example the wavelength selector 210 and wavelength reference 200. Software installed on the controller 270 performs spectroscopic calculations to quantify amounts of substances in the fluid samples, and provides the information on the graphical display 300 and/or sends output information to other instrumentation. Analog signals generated by the sensors 230 and 260 are converted to digital signals with the analog-to-digital converter 280. A radio frequency (RF) synthesizer 310 supplies a signal to a RF amplifier 290 which is used to control the AOTF crystal. A wavelength reference controller 320 is provided to control actuation of the wavelength reference 200 into the optical beam. The configuration of electronic components presented above is exemplary only, and those skilled in the art will understand that numerous configurations comprising a plurality of component and interconnection variations are within the scope of the invention.

Figure 4:
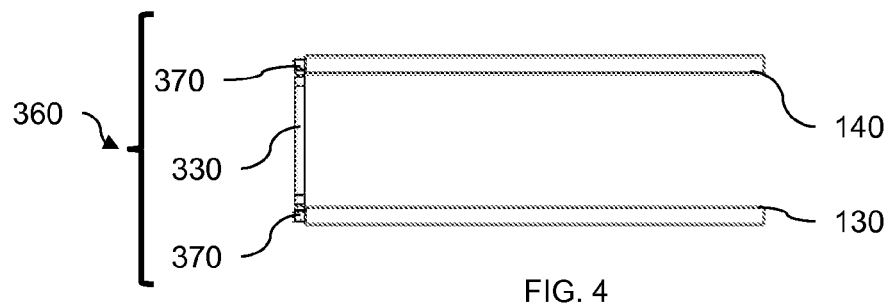
FIG. 4 is a side view of an embodiment of a tubing assembly.

Embodiments of the present invention provide for multiple optical sampling configurations, both by free-space and fiber optically coupled approaches. In one embodiment shown in FIGS. 4-6, a polymer fluid conduit 330 with a cartridge 340 and associated optical interface 350 are provided for fluid sampling. FIG. 4 shows the fluid conduit 330 connected to fluid delivery tubing assembly 130 and fluid return tubing assembly 140 by connectors 370. The fluid conduit 330 for optical sampling may comprise one or more polymers, and should be chosen such that at least a portion is generally transparent in the wavelength range of interest. Polymers for use in the near-infrared include Teflon® polytetrafluoroethylene (PTFE), ethylene tetrafluoroethylene (ETFE), Teflon® fluorinated ethylene propylene (FEP), Teflon® amorphous fluoroplastics (AF), modified fluoroalkoxy (MFA), and Teflon® perfluoroalkoxy copolymer (PFA). Such perfluorinated polymers commonly offer high transparency and few absorption features in the near-infrared. For use in wavelength ranges other than the near-infrared, the fluid conduit 330 may be comprised of a plurality of polymer and rubber tubing materials. Examples of such materials include polyethylene, polyether ether ketone (PEEK), polyvinyl chloride (PVC), nylon, and polycarbonate. The fluid delivery tubing assembly 130 and fluid return tubing assembly 140 may comprise tubing such as silicone, PharMed®, or Tygon®. The connectors 370 may comprise polymers, metals, or composites, and joints may be reinforced with for example adhesives, shrink tubing, or cable ties. Joints between the tubing sections may also be formed by welding, overmolding, or adhesive bonding. For biological or pharmaceutical applications, all tubing sections and connectors that are in contact with fluid samples should preferably be comprised of materials that can withstand sterilization by techniques such as autoclave, gamma irradiation, or ethylene oxide.

The cartridge 340 may be configured to house one or more tubing assemblies 360 comprising one or more fluid conduits 330. In one embodiment the cartridge 340 is preferably comprised of polymers such as polyethylene or polypropylene that are amenable to manufacturing by injection molding. Manufacturing cartridges 340 by mass production techniques such as injection molding provides for sufficiently low production costs to render the parts disposable. Components that are considered "single-use" or "disposable" are commonly used in one process and subsequently discarded. Such single-use components and assemblies are desirable in pharmaceutical and bioprocess applications where sterility is a primary concern. Single-use components commonly offer ease of sterilization as the contents are typically free of debris prior to sterilization as well as reduced labor costs as components do not require cleaning subsequent to processing. Cartridges 340 may also be comprised of other polymers, metals, composites, or combinations thereof and be designed to be single-use or multiple-use components.

Figure 5:
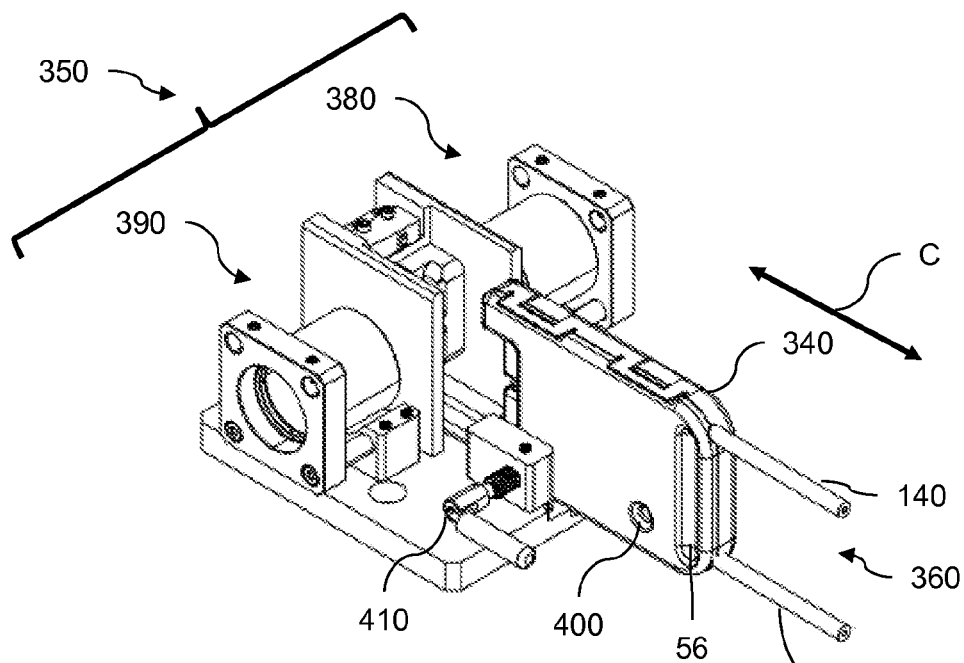
FIG. 5 is an isometric view of a disposable cartridge, tubing assembly, and optical interface for fluid sampling.
Figure 6:
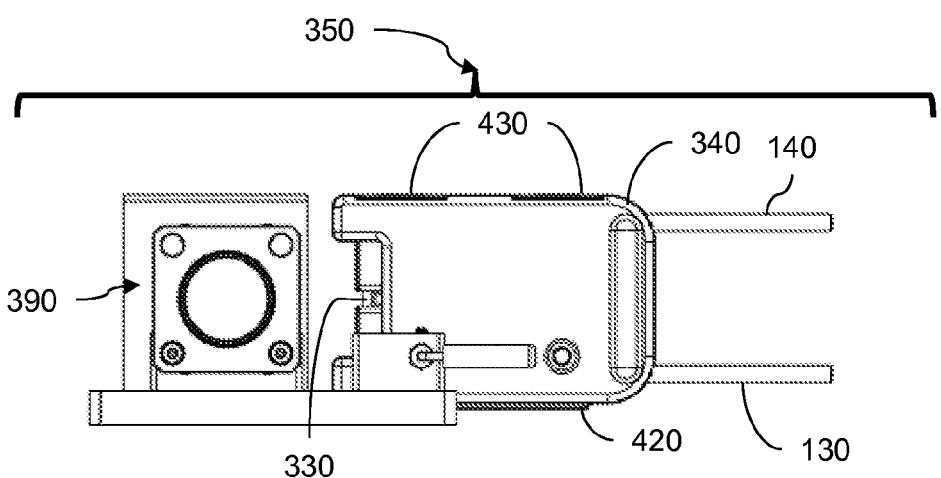
FIG. 6 is a side view of a disposable cartridge, tubing assembly, and optical interface for fluid sampling.

FIG. 5 shows the installation of a tubing assembly 360 housed within a cartridge 340 into the optical interface 350. The cartridge 340 may be installed or removed by translating the cartridge 340 containing the tubing assembly 360 along the direction indicated by double arrowed line C. The optical interface 350 comprises an input optical assembly 380 and output optical assembly 390. Each optical assembly may comprise one or more mechanical components such as lens tubes and support rods, as well as one or more optical components such as lenses. Optical and mechanical components may be chosen to best suit the wavelength range of interest. A locking pin recess 400 on the cartridge 340 and corresponding locking assembly 410 are provided to secure the cartridge within the optical interface 350. A side view of the optical interface 350 and cartridge 340 housing a tubing assembly 360 is shown in FIG. 6. In this embodiment, the cartridge 340 is shown with an integrated hinge 420 and snap features 430 to engage the cartridge when closed around a tubing assembly 360. Injection molding enables the cartridge 340 to comprise a single polymer component that is light weight, durable, and able to be sterilized by common methods. Embodiments of the present invention provide for use of multiple cartridges 340 in conjunction with a single optical interface 350, and may further comprise a means of selecting one cartridge from a group for optical interrogation of the fluid sample contained within one of the fluid conduits contained therein. Such a selection means comprises components to select, install, and remove cartridges 340 from an optical interface 350, and may be configured to do so in an automated fashion. The ability to provide measurement of fluid samples from multiple cartridges 340 in an automated fashion enables multiplexed measurements to be performed whereby a single optical instrument 110 may perform measurements on fluid samples from multiple vessels or from multiple locations within the same vessel.

Figure 7:
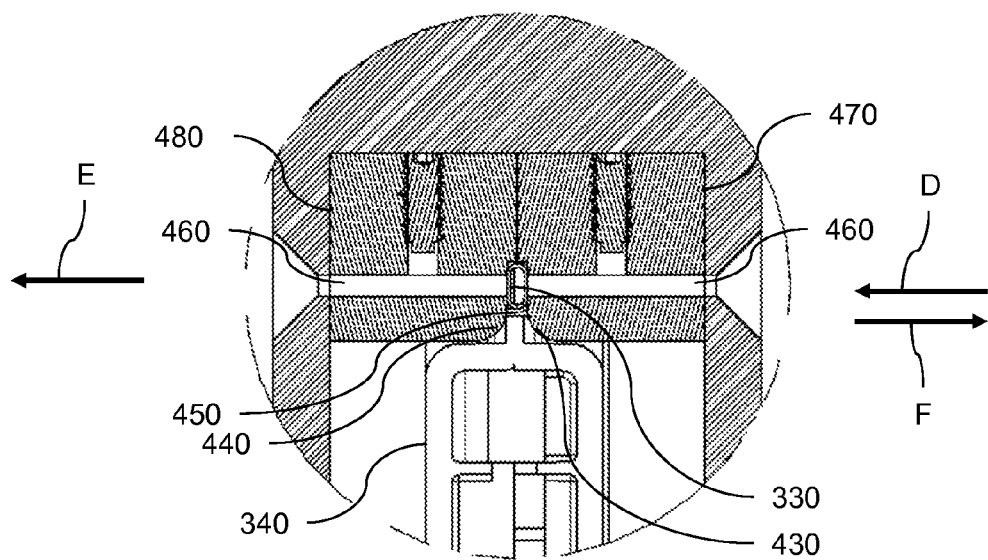
FIG. 7 is a detailed cross sectional view of an optical sampling interface.

In embodiments of the present invention, the optical interface 350 provides for establishing a defined optical path length through a fluid sample within a fluid conduit 330 by compressing the fluid conduit 330 to form a defined path length. A detailed cross sectional view of the portion of the optical interface 350 comprising the compression features is shown in FIG. 7. The cartridge 340 containing a fluid conduit 330 is shown installed within the optical interface 350. A defined optical path length is established by compressing the fluid conduit 330 between a first compression surface 430 of a first compression block 470 and a second compression surface 440 of a second compression block 480. Two optical waveguides 460 installed within the compression blocks 470 and 480 provide optical communication of light from the optical emitter 170 into the fluid conduit 330 and from the fluid conduit 330. The region between the optical waveguides 460 and compression surfaces 430 and 440 comprises a measurement zone 450 for optical sampling of a fluid. For example, light incident in the direction of arrowed line D may be communicated by one optical waveguide 460 into the fluid conduit 330 compressed between the first compression surface 430 and second compression surface 440. At least a portion of light having interacted with said fluid sample may be communicated from the fluid conduit 330 by another optical waveguide 460. A portion of light communicated from the fluid sample by optical waveguide 460 in a direction indicated by arrowed line E may be collected for example by an output optical assembly 390 to be communicated to other optical elements or a sensor 230. An optical arrangement whereby a portion of light incident in the direction of arrowed line D is communicated through a fluid conduit 330 and light having traveled through a fluid sample contained within the fluid conduit 330 is subsequently communicated in the direction of arrowed line E to a sensor provides an optical transmission measurement. An optical transflection measurement may also be provided by the current invention. In this configuration, a portion of light incident in the direction of arrowed line D is communicated by an optical waveguide 460 into a fluid sample within a fluid conduit 330, and a portion of light having interacted with the fluid sample is communicated by the same optical waveguide 460 in a direction indicated by arrowed line F. Light returning in the direction of arrowed line F will generally comprise portions that have transmitted through the fluid sample and reflected off the second optical waveguide 460 or an alternative optical element positioned to reflect a portion of the light. The optical waveguides 460 may comprise for example hollow waveguides, optical fibers, optical rods, or optical windows. In the near-infrared spectral range, materials such as reflective elements, zinc selenide (ZnSe), germanium, sapphire, silicon, BK7 optical glass, B270 optical glass, low hydroxyl silica, and other glasses with low hydroxyl content may be used. Surfaces of the optical waveguides 460 in proximity to the measurement zone 450 may be coplanar with the compression surfaces 430 and 440 or offset. In a configuration where the surfaces of the optical waveguides 460 are coplanar with the compression surfaces 430 and 440 or offset into the measurement zone 450, said surfaces of the optical waveguides 460 may also provide definition of the optical path length by compression of the fluid conduit 330. The optical path length defined by the compression surfaces 430 and 440 and optical waveguides 460 may be set by defining the distance between said compression surfaces. The length of the optical path within a fluid sample when the optical interface 350 is in a transmission optical configuration is generally the distance that light travels between the compression surfaces 430 and 440 or optical waveguides 460 minus twice the wall thickness of the fluid conduit 330. It should be understood that a plurality of optical path lengths may be presented depending on the geometry of the compression surfaces, and that a distribution of optical path lengths may be provided by a configuration. A wide range of optical path lengths may be provided by embodiments of the present invention, and path lengths generally ranging from 0.2 mm to 5.0 mm are typical. In one embodiment, the optical path length is between 0.8 to 1.2 mm. The optical path length is typically determined by the available optical power, the absorption by water and other solvents in the fluid sample, and the scattering by suspended materials such as cells in the fluid sample. Embodiments of the invention are provided whereby the optical path length is adjustable, either manually or automatically, in order to accommodate a plurality of fluid samples with differing characteristics. For example, if optical attenuation by a fluid sample is sufficiently high to degrade system performance, the path length may be shortened to reduce the attenuation and increase optical signal intensity. Embodiments are also provided wherein electromagnetic radiation is communicated by free-space coupling whereby no optical waveguides are utilized.

Figure 8:
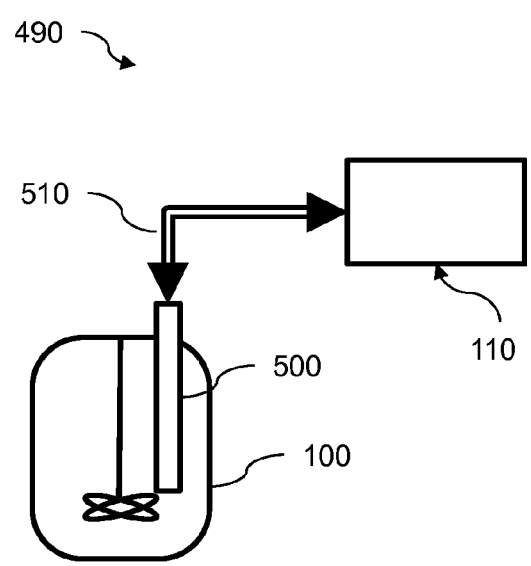
FIG. 8 is a block diagram of the invention utilizing a fiber optically coupled interface.
Figure 9:
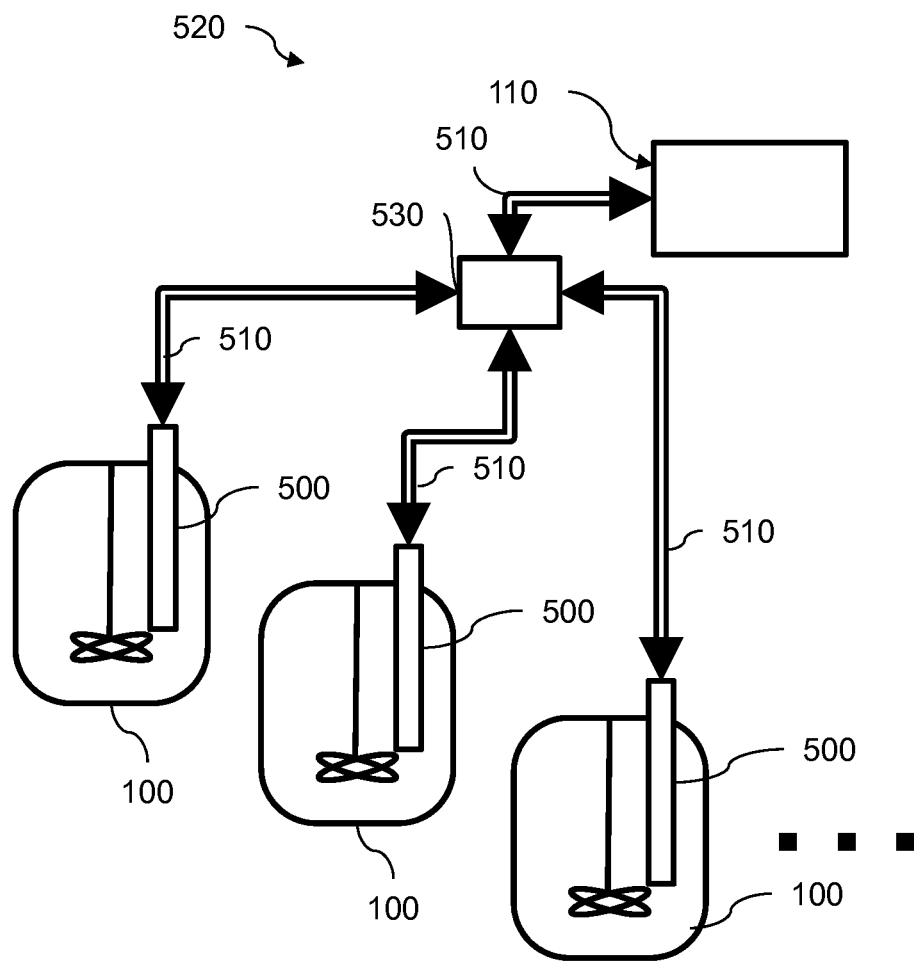
FIG. 9 is a block diagram of the invention configured to perform multiplexed measurements of multiple fluid processes.

Optical sampling of fluid samples may also be provided by one or more fiber optically coupled interfaces that are installed at least partially within a vessel. Vessels interrogated by fiber optically coupled interfaces include for example multiple-use vessels such as stirred tank bioreactors as well as single-use vessels such as bag bioreactors and mini- and micro-bioreactors. One such embodiment of sampling with a fiber optically coupled interface wherein the interface is a probe is shown in the block diagram in FIG. 8. In this embodiment providing a single-probe configuration 490, an optical probe 500 is installed within a vessel 100 such that optical elements within the optical probe 500 are in fluid contact with the contents of the vessel 100 during fluid processing. One or more optical fibers 510 connect the optical instrument 110 to the optical probe 500. In an embodiment where the optical probe 500 is configured for a transmission optical measurement, two optical fibers 510 may be provided for each optical probe 500. In such a configuration, the optical probe 500 is preferably configured for a single-pass transmission measurement. Light from the optical instrument 110 is optically coupled to the optical probe 500 by at least one optical fiber 510 where at least a portion of light interacts with a fluid in the vessel 100, and at least a portion of the light having interacted with said fluid is communicated to the optical instrument 110 by an optical fiber 510 and sensed by a sensor 230. For use with sterile processes such as bioprocessing, optical probes 500 should preferably be designed to withstand sterilization by one or more standard processes such as autoclave, gamma irradiation, and ethylene oxide treatment. Due to the need to connect optical probes to the optical instrument 110 by optical fibers 510, the NIR emitter 180 should preferably be a high brightness emitter, such as a semiconductor light source, amenable to fiber optic coupling as described above. Various implementations of the present invention provide for multiplexed measurements whereby a single optical instrument 110 is used in conjunction with multiple optical interfaces, such as probes 500, to measure fluid samples from multiple vessels or from multiple locations within a single vessel. An embodiment showing a single optical instrument 110 configured to perform measurements in multiple vessels 100 is shown in FIG. 9. In this multiplexed probe embodiment 520, a fiber optic switch 530 is connected to the optical instrument 110 by one or more optical fibers 510, and one or more optical fibers 510 optically communicate with one or more fiber optic probes 500 each with one or more optical fibers 510. A fiber optic switch 530 may also be integrated within an optical instrument 110. Fiber optic probes 500 may be provided with a plurality of optical path lengths as with the optical interface 350, generally in the range of 0.2 mm to 5.0 mm. Embodiments of the invention are also provided where optical emitters and/or sensors may be integrated within fiber optic probes. Embodiments are also provided without a fiber optic switch, whereby multiplexed measurements are provided by multiple optical emitters and sensors within an instrument.

Figure 10:
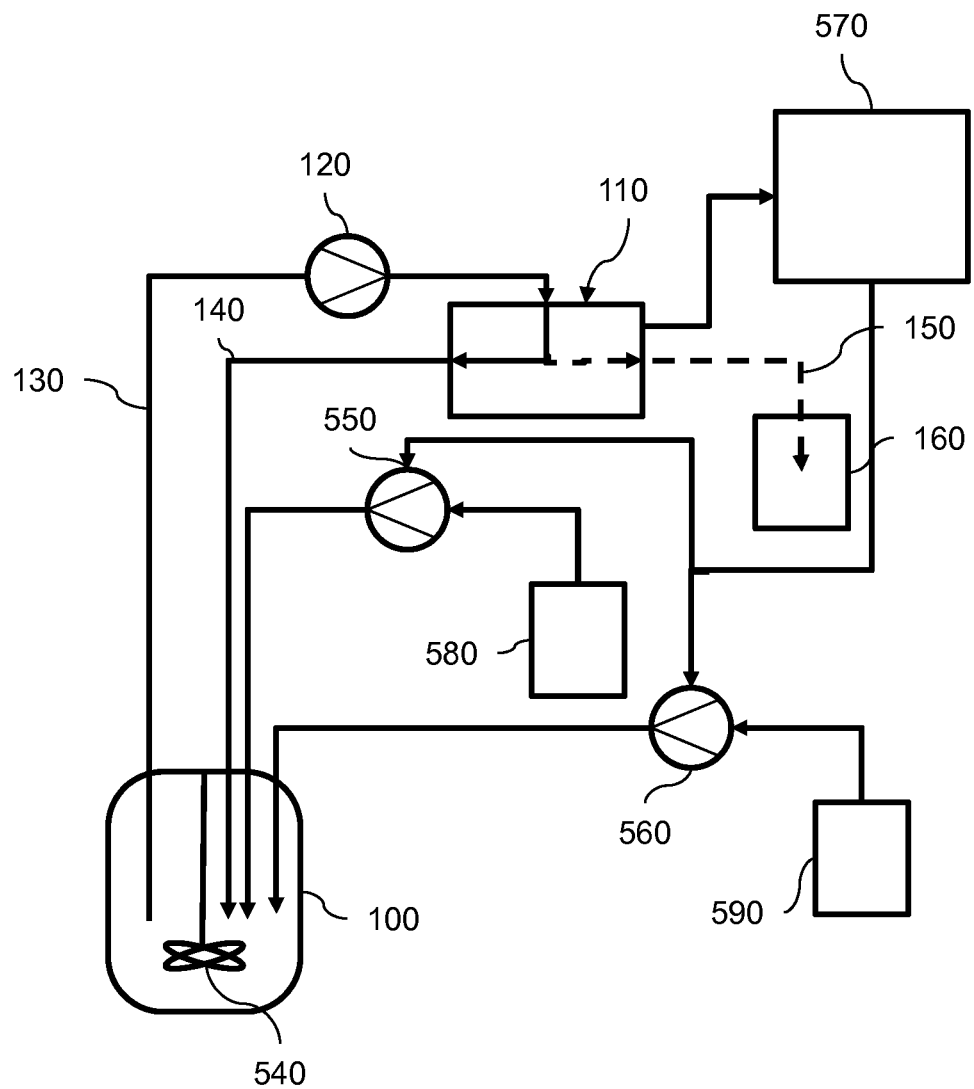
FIG. 10 is a block diagram of the invention configured to perform feedback control of multiple substance concentrations in a fluid process.

In addition to the ability to measure quantities of multiple substances in fluid samples, certain implementations of the present invention provide for feedback control of the quantities of substances or the values of parameters in fluid processes. In one such embodiment, measurements of one or more quantities of substances in a fluid sample from a fluid process are used to control the values of one or more parameters in a fluid process. Quantities such as concentrations of chemical constituents, turbidity, or cell density determined by the optical instrument 110 may be used as inputs to control parameters of the fluid process such as agitation rate, the level of dissolved oxygen in the fluid, the pH of the fluid, the temperature of the fluid, and level of foaming within the vessel 100. FIG. 10 shows one embodiment where the present invention may provide for control of multiple parameters or quantities of substances within a fluid process. For example, the present invention may be configured to change the agitation rate within the vessel 100 by adjusting the speed of the agitator 540 when the measured cell density reaches a specified level. In another example, the present invention may provide control of antifoam additions to the fluid process in response to measurements of cell density or chemical constituent concentration. In another example, the present invention may be used to control the temperature of the fluid process in response to measurements of cell density or chemical constituent concentration. This functionality may be provided directly by optical instrument 110, whereby the parameter is controlled by the NIR optical instrument 110, or whereby the NIR optical instrument 110 may provide output signals to a process controller 570 that accepts said output signals as inputs and controls the parameters of the fluid process.

Embodiments of the present invention provide for feedback control of chemical constituent concentration, either directly or in conjunction with a process controller 570. Feedback control of chemical constituent concentration in a fluid process is provided by comparing a measurement performed with the NIR optical instrument to a desired concentration level or concentration level profile. Based upon the difference in the measured concentration value to the desired concentration value or concentration profile, a signal may be provided to a transfer pump 550 that transfers a quantity of a substance at least partially comprising the measured chemical constituent from a source container 580 to the fluid process in the vessel 100. Concentrations of more than one chemical constituent may be controlled by implementations of the present invention, for example a second transfer pump 560 may be used to transfer a quantity of a substance at least partially comprising a second measured chemical constituent from a second source container 590 to the fluid process in the vessel 100. Control of parameters in the fluid process or concentrations of chemical constituents may be performed with the present invention in a plurality of configurations. Circulation of one or more fluid samples with pumps 120, fluid delivery tubing assemblies 130 and fluid return tubing assemblies 140 or fluid exhaust lines 150 and waste containers 160 may be provided. Alternatively, fluid sampling in control configurations may be performed with fiber optically coupled interfaces as with embodiments 490 and 520 in FIG. 8 and FIG. 9.

Methods for determining quantities of substances within fluid samples in biological and other processes, as well as for providing control of such processes, are presented in the following description. A beam of near-infrared electromagnetic radiation is provided by an optical emitter, said optical emitter may comprise a broad bandwidth emitter such a tungsten halogen bulb, or an emitter having a narrower bandwidth such as a semiconductor emitter. A tungsten halogen bulb or other thermal emitter typically exhibits an optical emission spectrum resembling a black body emission spectrum. Such an emission spectrum is generally broad in extent, and may provide electromagnetic radiation output for example from the visible spectrum into the infrared. In implementations of the present invention optical emitters having electromagnetic radiation emission generally within the wavenumber range including 3300 $cm^{-1}$ to 14,000 $cm^{-1}$ (corresponding to 0.7 to 3.0 µm in wavelength) are preferable. Near-infrared light may also be provided by an optical source having an emission spectrum generally narrower than a thermal source, for example a semiconductor optical source. Semiconductor optical emitters commonly exhibit emission spectra narrower than thermal sources, and the emission characteristics are often configurable. Light emitting diodes, superluminescent diodes, and tunable laser diodes are examples of such semiconductor optical emitters. Semiconductor light sources may be provided with generally fixed emission characteristics such as with LED and SLD sources, or with tunable emission characteristics such as with a TLD. A TLD emitter assembly comprises a semiconductor element configured to emit light at desired wavelengths, and may further comprise tuning optics external to the semiconductor element. Tuning optics may comprise for example a grating, AOTF crystal, or other wavelength selection means as well as other optical elements configured to enable tuning or variation of the emission characteristic.

Electromagnetic radiation generated by a broadband optical source or a semiconductor optical emitter may be directed into a wavelength selector. Said wavelength selector may be configured to select one or more segments of the electromagnetic radiation, and is commonly configured to select a plurality of segments of electromagnetic radiation in order to enable spectroscopic measurements to be performed over a desired wavelength range. The wavelength selector may comprise an AOTF, a planar reflection diffraction grating, a non-planar reflection diffraction grating, or a transmission diffraction grating. The present invention provides for placement of the wavelength selector in numerous locations within the optical path—before or after the fluid sample. As described above, the wavelength selector may also be located within an optical emitter assembly to provide a tunable optical emitter. While it is common in the art to provide optical instruments with high spectral resolution, in the present invention the resolution of the wavelength selector may in certain implementations be poorer than 8 $cm^{-1}$. As the samples of interest are generally fluid samples, often being aqueous fluid samples, the spectral features are generally broader than 8 $cm^{-1}$, often broader than 30 $cm^{-1}$, resolution of the wavelength selector may be poorer than 8 $cm^{-1}$.

Certain implementations of the present invention provide a wavelength reference means comprising a polymer optical element. Spectroscopic analysis of fluids and materials contained therein commonly requires the wavelength axis to be well known if accurate quantification is to be provided. Known spectral characteristics of substances within fluids, such as chemical constituents, are commonly used in the determination and quantification of concentrations or levels of such substances—if the wavelength axis of a spectroscopic measurement is offset, skewed, or otherwise distorted, measurement errors may result. Wavelength reference or calibration means provided in the prior art commonly utilize a single wavelength or narrow wavelength band as a standard, such as a laser, bandpass filter, or other apparatus or material with narrow spectral features. In such configurations the reference or calibration is generally performed by peak fitting to one or few spectral features, and while this may provide an adequate calibration if there is a simple shift in the wavelength axis that is uniform across the spectral range of interest, the calibration may be unsatisfactory if there is skew or other distortions in the wavelength axis. Utilization of a polymer optical element may provide a broad bandwidth wavelength reference whereby shift, skew, and other distortions in the wavelength axis may be corrected. A polymer optical element used for wavelength calibration purposes is preferably at least partially transparent over the wavelength range of interest, and the absorption characteristic of the polymer optical element should differ between at least two wavelengths in order that there is a spectral feature for the purpose of comparing to a reference spectrum. The polymer optical element will preferably have one or more distinct spectral absorption features within the wavelength range of interest to which a comparison may be made. In embodiments of the present invention, a transmission spectrum of the polymer optical element is compared to a reference transmission spectrum by a regression operation performed over the entire wavelength range of interest. By performing the wavelength reference operation over the entire wavelength range of interest, both shifting and scaling operations may be performed on the wavelength axis. The ability to both shift and scale the wavelength axis over the entire wavelength range of interest provides a well-defined wavelength axis permitting robust spectroscopic measurements to be performed. Wavelength reference operations may be performed continuously whereby the polymer optical element is positioned in an optical path throughout operation, or intermittently whereby the optical element is inserted into an optical path with an actuator. Such continuous or intermittent adjustment or calibration of the wavelength axis of the measurement provides for higher measurement accuracy and mitigates against drift due to environmental fluctuations or other perturbations to the fluid measurement instrument. Embodiments of the present invention provide for performing a plurality of wavelength reference operations throughout a fluid process. For example, a wavelength reference operation may be performed every 30 minutes during fluid processing wherein the fluid process lasts for a period of time of one week or more. Ideally, the absorption properties of the reference polymer are insensitive to environmental variations, most notably temperature and humidity.

At least a portion of the electromagnetic radiation generated by the optical emitter is directed to a fluid sample within a fluid sampling interface or fiber optically coupled interface where said electromagnetic radiation may interact with said fluid sample and substances contained therein by processes such as absorption and scattering. The fluid sample interrogated is commonly not homogeneous, and may contain a plurality of fluid components and suspended materials. As certain implementations of the present invention provide for performing measurements in the near-infrared region of the electromagnetic spectrum where an optical transmission band exists in water, fluid samples may be generally aqueous in composition. The fluid sampling interface typically provides a length of optical path through the fluid sample contained therein in the range of 0.2 mm to 5.0 mm. This optical path length generally determines the interaction length whereby the electromagnetic radiation may interact with the fluid sample and materials contained therein. Fluid sampling interfaces may be free-space optically coupled or utilize optical fibers for delivery and collection of light to and from a fluid sample. Free-space optically coupled examples of the fluid sampling interface typically comprise a fluid conduit, said fluid conduit being at least partially transparent in the wavelength range of interest. Fluid sampling interfaces employing fiber optic coupling comprise one or more optical fibers configured to perform at least one of communication of electromagnetic radiation to a fluid sample and communication of electromagnetic radiation having interacted with said fluid sample to an instrument. In one embodiment, the fiber optically coupled fluid sampling interface comprises at least one optical probe immersed in a fluid, said probe being in optical communication with an instrument by means of at least one optical fiber. Both free-space and fiber optically coupled fluid sampling interfaces may be configured to operate in a transmission or transflection optical geometry. In a transmission configuration, electromagnetic radiation incident on a fluid sample passes through said fluid sample once, and a portion of said electromagnetic radiation is collected. In a transflection configuration, a portion of electromagnetic radiation incident on a fluid sample passes through said fluid sample and is directed back through the fluid sample to be collected generally in the incident direction, and a portion of the electromagnetic radiation reflects off the fluid sample and materials therein, and is collected generally in the incident direction. Embodiments of the present invention may additionally comprise an additional analysis module for further characterization of fluid samples by optical or non-optical means. Fluid delivery to such an additional analysis module may be performed by the same fluid conduit used in the near-infrared optical measurement, or by an additional fluid conduit. Examples of such analysis modules include means of performing electrochemical analyses, fluorescence measurements, ultraviolet and visible optical measurements, and Raman scattering analyses.

Electromagnetic radiation having interacted with a fluid sample is collected and communicated to at least one sensor and used to determine at least one quantity of a substance within said fluid sample. Determination of quantities of substances within fluid samples is performed by scrutiny of the spectrum of electromagnetic radiation having interacted with a fluid sample. In one embodiment a second sensor is provided in a second optical path, said second sensor being configured to sense electromagnetic radiation not having interacted with said fluid sample. A second sensor configured to sense electromagnetic radiation not having interacted with a fluid sample may provide a reference or blank signal by which a reference measurement can be performed. Such a reference measurement enables mitigation of drift in instrument performance due to variation in environmental conditions or instrument component parameter fluctuations. Sensors provided in the present invention may be single-element sensors or multi-element sensors such as array sensors in various implementations.

Various implementations of the present invention provide for determination of a plurality of quantities of substances within fluid samples, and commonly such quantification may be performed on multiple substances simultaneously. Given the near-infrared absorption characteristics of substances containing C—H, C—O, S—H, O—H, P—H, and N—H bonds, measurement of the quantities or concentrations of many such substances in fluids samples is provided. Absorption characteristics in the near-infrared spectral range of alcohols, sugars, lipids, organic acids, amino acids, fatty acids, peptides, DNA, and proteins permit determination of quantities of such substances in fluid samples. Specific chemical constituents for which certain implementations of the present invention may provide measurement include, but are not limited to, glucose, glycerol, methanol, ethanol, lactate, acetate, and ammonium. Quantities and concentrations of materials suspended in fluid samples such as cells and particles may also be determined with certain implementations of the present invention. Scattering and absorption of electromagnetic radiation due to interaction with such suspended materials alters the characteristics of electromagnetic radiation used to interrogate fluid samples, thus providing means to determine quantities of such substances. Cell density and fluid turbidity may be measured with certain implementations of the present invention, and information on cell viability may be provided as well. Due to the morphological differences between live cells and dead cells, the optical scattering properties differ as well, permitting extraction of information on cell viability. Such cell density and viability information is highly valuable particularly in biological and pharmaceutical research and manufacturing applications. As the present invention utilizes electromagnetic radiation in the near-infrared spectral range, attenuation of the optical beam interrogating a fluid sample due to scattering from suspended materials is substantially reduced compared to technologies utilizing shorter wavelength light owing to the fact that the intensity of optical scattering process typically scales as the inverse of the wavelength to the fourth power. Certain embodiments of the present invention provide for determination of quantities or concentrations of more than one of the substances and materials listed above simultaneously. Certain embodiments of the present invention may feature automatic rejection of NIR spectra that are sufficiently contaminated by entrapped gas bubbles.

Analysis of the collected fluid sample spectrum can be performed to ascertain when a given spectrum falls outside of acceptable bounds and is thereby flagged as contaminated with air, and rejected from further data processing or display to the user.

Quantities of substances within fluid samples may be measured intermittently or continuously with various embodiments of the present invention. Continuous measurements of substances in fluid samples is particularly advantageous for numerous fluid processes and applications, as conditions within the fluid process and quantities or concentrations of substances often change throughout a process, and often on short time scales such as several minutes. Fluid processes such as bioprocesses and chemical processes are examples of such processes where continuous monitoring of substances is advantageous. Embodiments of the present invention are well-suited to performing continuous optical measurements in for example yeast fermentations, bacterial processes, insect cell cultures, mammalian cell cultures, and protein expression processes. Bacterial bioprocesses, for example *E. coli* processes, are examples of such processes where properties of fluids and materials contained therein change rapidly. In bioprocesses, implementations of the present invention provide for performing measurements in the cell growth stage, the product formation stage, the product purification stage, and the product formulation stage of the process. Fluid processes from which fluid samples to be measured are obtained may be batch processes, semi-continuous processes, continuous processes, or perfusion processes. Processes may be monitored in real-time with certain embodiments of the present invention—the measurement frequency may be greater than one measurement per minute, and each measurement may provide quantification of one or more substances. Continuous monitoring of fluid processes with certain implementations of the present invention provides not only measurements of substances in fluid samples with high time resolution, but also the ability to detect outlier conditions in processes, provide a means of quality control, and enable feedback control of such processes.

Methods concerning various embodiments of the present invention may further comprise steps providing feedback control and associated operations in bioprocesses and other fluid processes. The present invention may provide means for control of parameters of a fluid process, or control of quantities or concentrations of substances within a fluid process. Measurement of quantities of substances in or materials suspended in a fluid sample, such as chemical constituents or cell density, may be used to adjust one or more parameters or quantities in the fluid process from which the fluid sample originates. As an example of parameter adjustment and control, a measured quantity such as cell density in a process may be used to adjust a parameter such as agitation rate or dissolved oxygen level. For instance, upon reaching a specified cell density, agitation rate or dissolved oxygen level may be increased to support the oxygen demands of the growing cell population. Parameters such as temperature and pressure of fluid process may also be controlled. Foaming within a vessel may also be mitigated by control of antifoam addition, for example when the cell density reaches a specified value.

Control of quantities or concentrations of substances such as chemical constituents in fluid processes may be provided by determining one or more quantities of substances and using said one or more determined quantities to adjust one or more quantities or concentrations. Such feedback control strategies are highly valuable in many applications to maintain desired quantities or concentration profiles of substances during fluid processes and to reduce the labor involved with providing such functionality manually. A target concentration or concentration profile may be controlled with embodiments of the present invention based not only upon one or more measured quantities, but also upon one or more consumption rates of substances, said consumption rates of substances being determined by the measured quantities of those substances. Cell growth rate may also be used to control a quantity or concentration profile of one or more substances in a fluid process. Process adjustments such as parameter values and quantities, concentrations, or concentration profiles of substances may also be provided by additional analyses. Analyses such as electrochemical, fluorescence, ultraviolet-visible spectroscopy, and Raman scattering may be provided for such process adjustments in conjunction with the near-infrared measurement provided.

Figure 11:
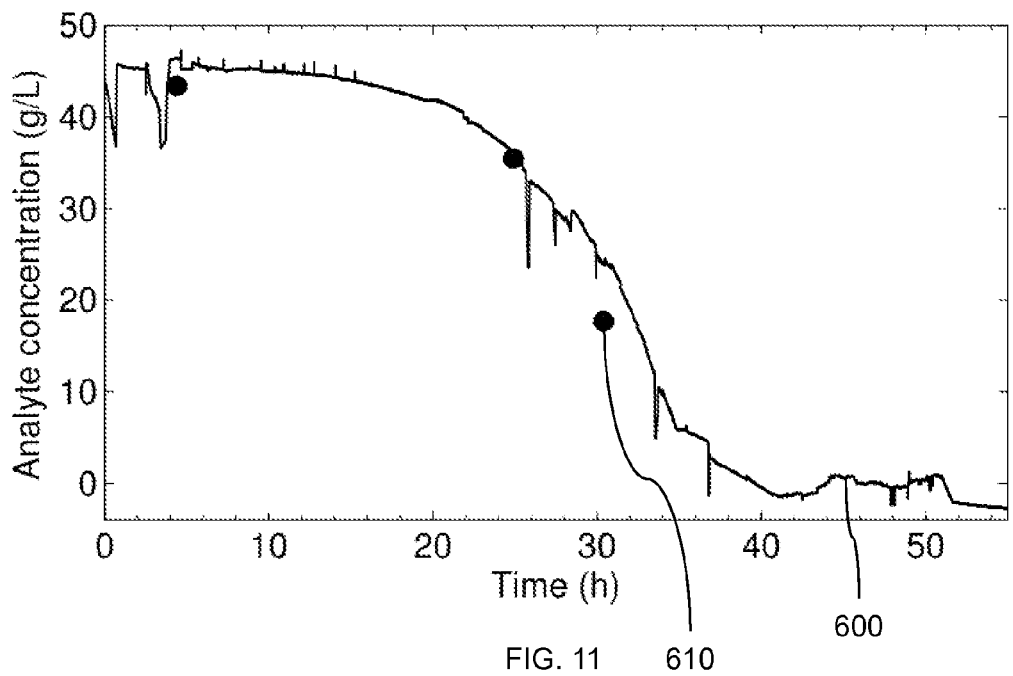
FIG. 11 is a concentration plot showing glycerol concentrations in a *Pichia pastoris* fermentation measured continuously by an implementation of the present invention (solid line) and discrete off-line reference measurements (circles).
Figure 12:
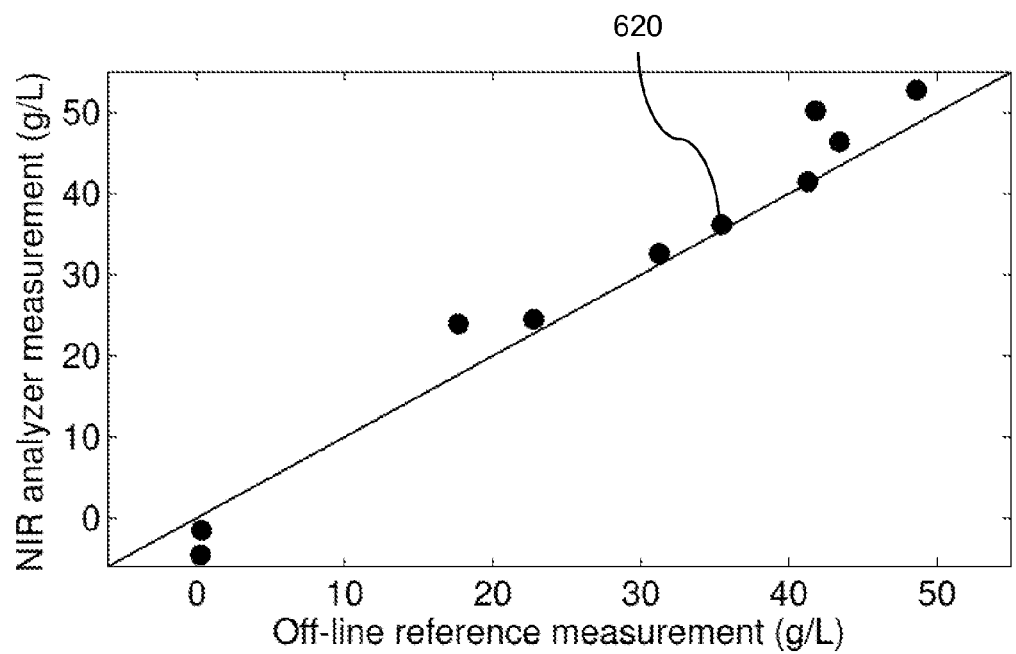
FIG. 12 is a plot showing the correlation between glycerol measurements performed with an embodiment of the present invention and off-line reference measurements.
Figure 13:
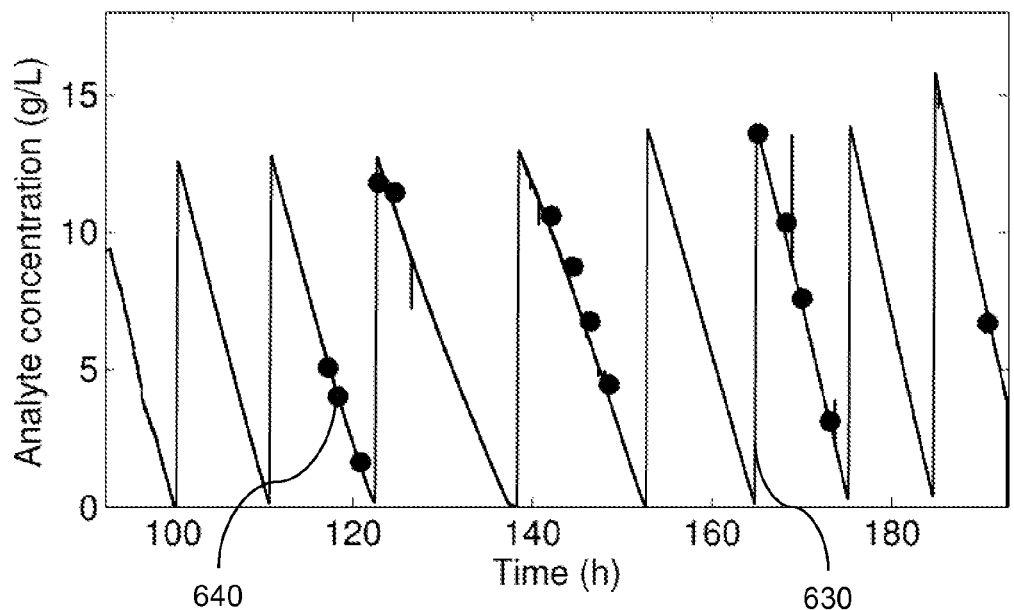
FIG. 13 is a concentration plot showing methanol concentrations in a *Pichia pastoris* fermentation measured continuously with an embodiment of the present invention (solid line) and discrete off-line reference measurements (circles).
Figure 14:
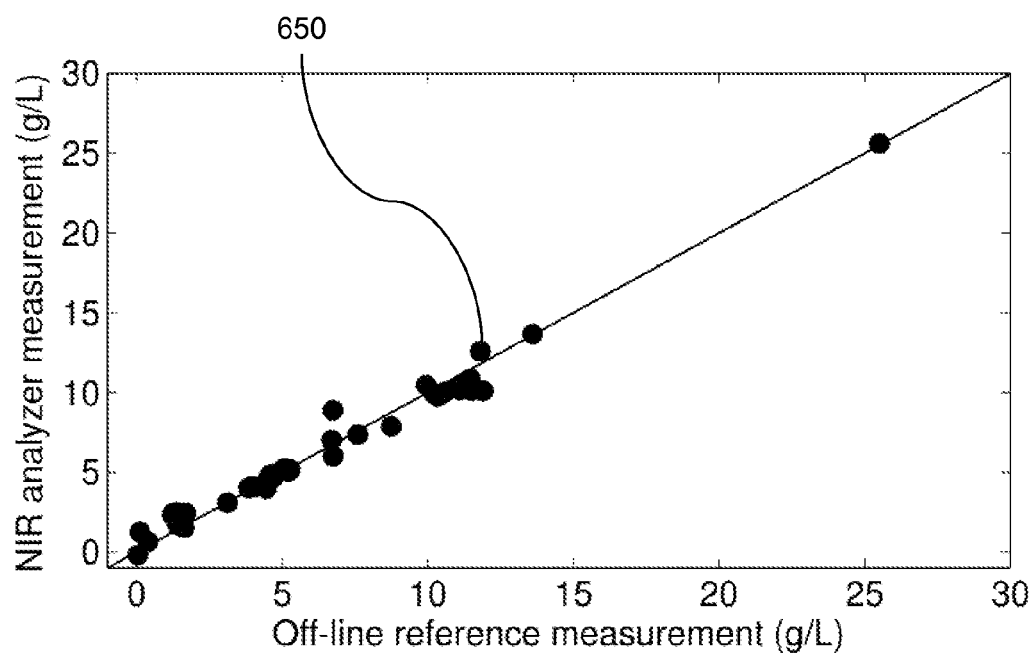
FIG. 14 is a plot showing the correlation between methanol measurements performed with an embodiment of the invention and off-line reference measurements.
Figure 15:
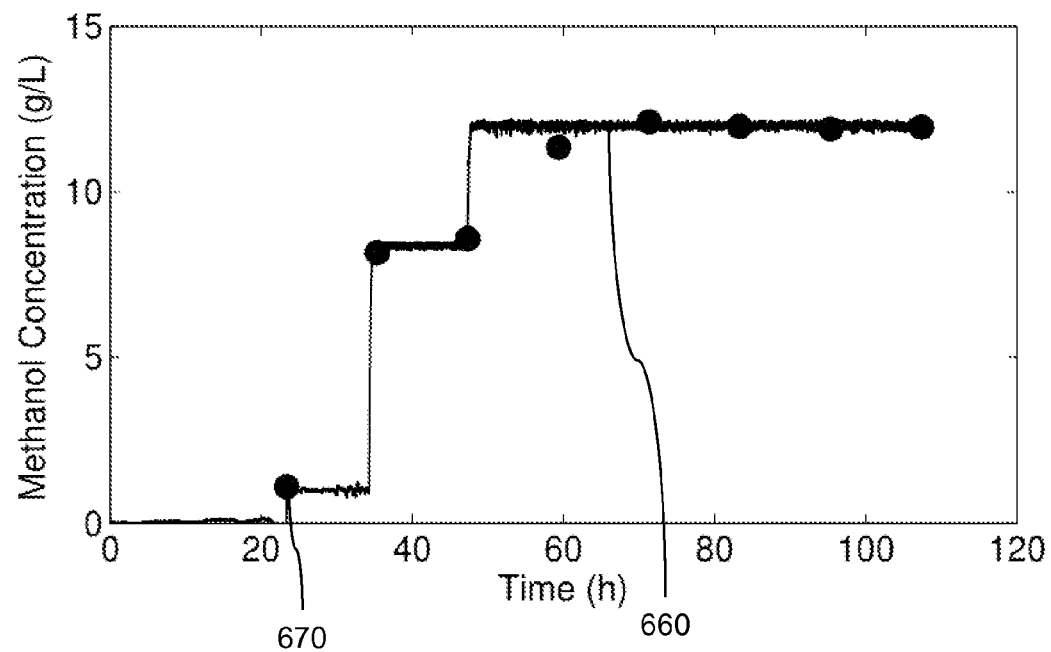
FIG. 15 is a concentration plot showing methanol concentrations in a *Pichia pastoris* fermentation with an embodiment of the present invention configured to provide feedback control of the methanol concentration. The measurements made with an embodiment of the present invention (solid line) are shown with off-line reference measurements (circles).
Figure 16:
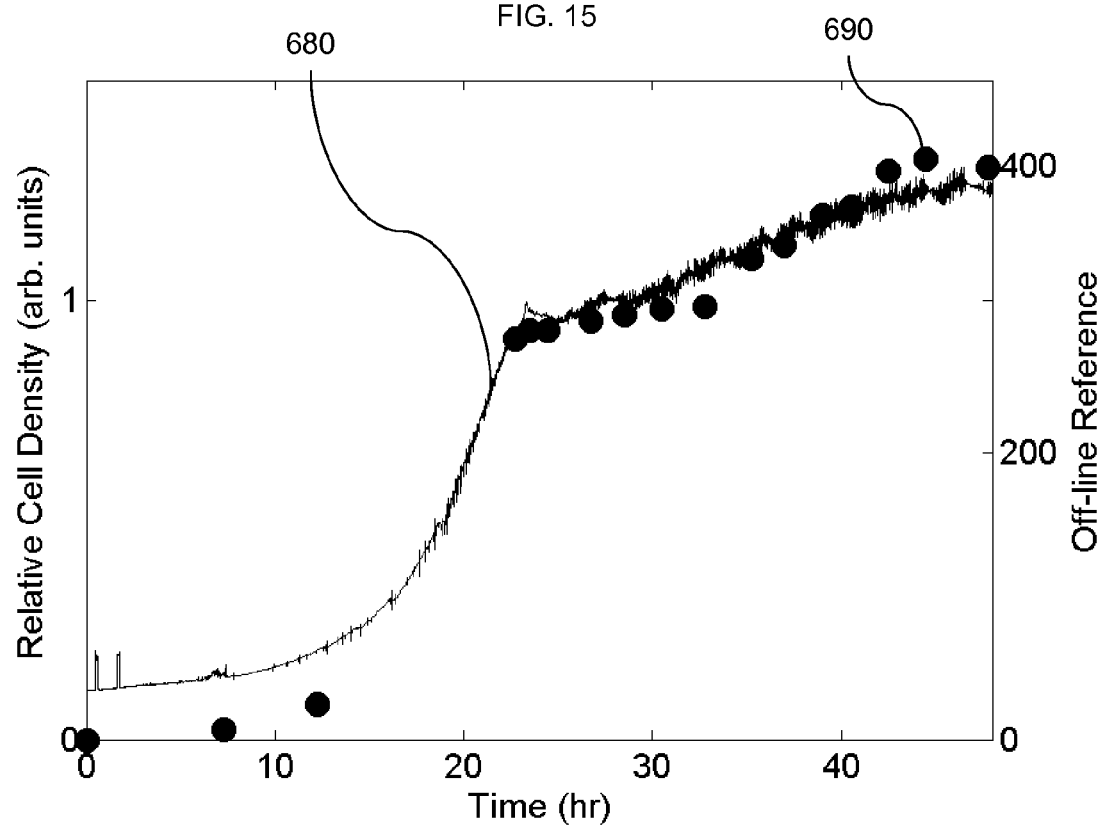
FIG. 16 is a plot of relative cell density measured by an embodiment of the present invention (solid line) and off-line reference measurements (circles).

A plurality of experiments has been performed with certain implementations of the present invention to demonstrate the utility of the invention. A concentration profile of glycerol during a portion of a *Pichia pastoris* fermentation is shown in FIG. 11. In FIG. 11, the line 600 represents the concentration measured as a function of time, and the circles 610 are independent reference measurements performed off-line. The correlation plot shown in FIG. 12 compares glycerol measurements taken with an implementation of the present invention optical apparatus to measurements taken as off-line reference measurements; each comparison is shown as a filled circle 620. The concentration profile 630 and off-line reference measurements 640 for a second chemical constituent, methanol, in a portion of a *Pichia pastoris* fermentation process are shown in FIG. 13. The correlation plot showing the accuracy of the measurements provided in comparison to off-line reference measurements is shown in FIG. 14 where circles 650 represent individual measurements. The concentration profile in FIG. 13 highlights the accurate measurements provided across numerous bolus doses of methanol to the process. Feedback control of constituent concentration is demonstrated in FIG. 15. The measured concentration profile of methanol provided by an implementation of the present invention 660 (solid line) is shown with off-line reference measurements 670 (circles). The tested implementations of the present invention provide continuous measurements over extended time periods, and have been demonstrated with fluid processes exceeding three weeks in duration. Relative cell density or biomass measurements are also provided. Knowledge of cell density is often highly desirable in cell culture and fermentation processes—both relative and absolute measurements are typically useful, as trend information lends key insights into process dynamics. FIG. 16 shows a relative cell density plot 680 measured with an implementation of the present invention (solid line) as well as off-line reference measurements 690 (circles). Off-line reference measurements were performed with a visible spectrometer, and are given as optical density at 600 nm (OD600).

Figure 17:
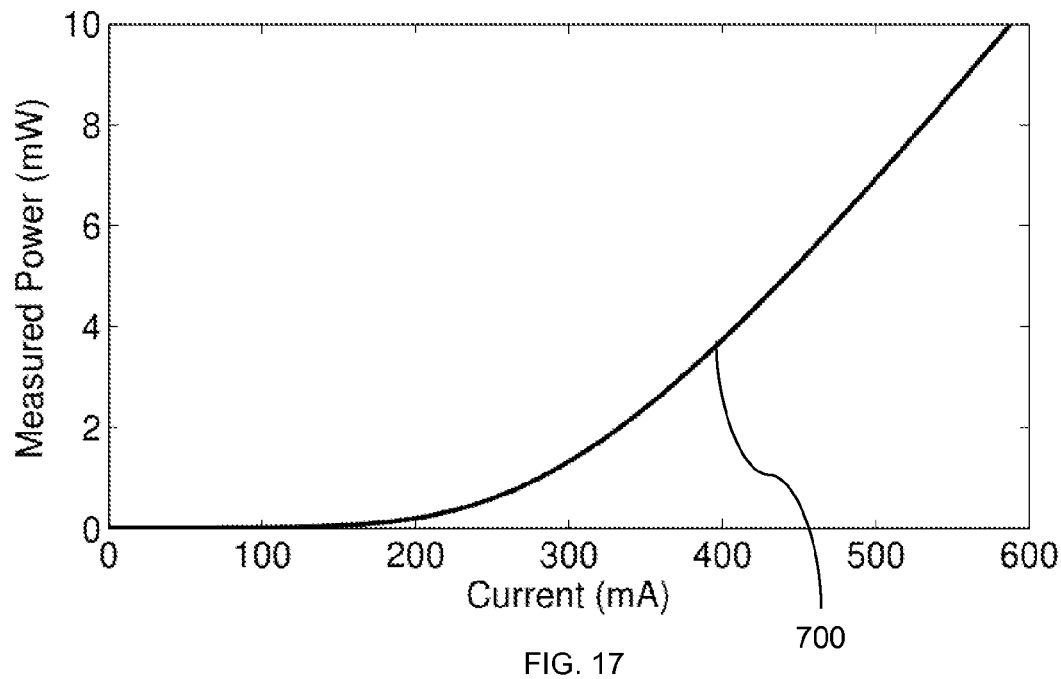
FIG. 17 is a plot of the current input vs. light output characteristic of a near-infrared superluminescent diode used as an optical emitter in an embodiment of the present invention.
Figure 18:
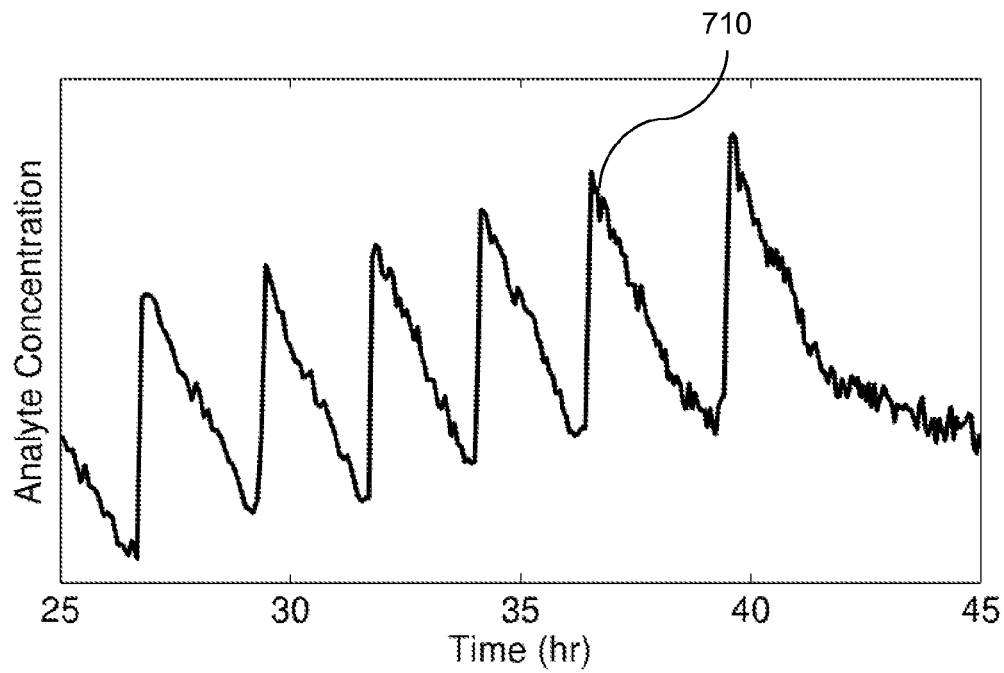
FIG. 18 is a concentration plot showing methanol concentrations in a *Pichia pastoris* fermentation with an embodiment of the present invention configured with a near-infrared superluminescent diode as the optical emitter.

Experiments were also performed with semiconductor light sources used in certain implementations of the present invention. A plot showing a current input vs. light output characteristic 700 for a superluminescent diode operating in the near-infrared with a peak wavelength of approximately 2.3 µm is shown in FIG. 17. High optical powers, exceeding 8 mW, were produced from this semiconductor light source which was used for performing measurements of chemical constituents in *Pichia pastoris* fermentation processes. A concentration profile 710 of methanol measured with a superluminescent diode light source in the apparatus during a *Pichia pastoris* fermentation processes is shown in FIG. 18. In this figure, measurement of multiple bolus doses of methanol are shown.

The present invention has been described with reference to the foregoing specific implementations. These implementations are intended to be exemplary only, and not limiting to the full scope of the present invention. Many variations and modifications are possible in view of the above teachings. The invention is limited only as set forth in the appended claims. All references cited herein are hereby incorporated by reference to the extent not inconsistent with the disclosure herein. Unless explicitly stated otherwise, flows depicted herein do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims. Any disclosure of a range is intended to include a disclosure of all ranges within that range and all individual values within that range.

The invention claimed is:

1. An apparatus for fluid analysis, said apparatus comprising:
   a. a near infrared electromagnetic radiation source;
   b. an optical wavelength selector positioned in an optical path from the near infrared electromagnetic radiation source, and configured to select one or more spectral segments of the near infrared electromagnetic radiation;
   c. a wavelength reference material positioned in the optical path and comprising at least one polymer optical element, said polymer optical element being at least partially transparent in at least a portion of a near infrared spectral range and exhibiting an absorption spectrum that differs in magnitude between at least two wavelengths;
   d. a fluid sampling interface positioned in the optical path;
   e. a sensor positioned at a termination of the optical path; and
   f. a controller configured to determine the quantity of one or more substances in a fluid sample based upon the measured spectrum of near infrared electromagnetic radiation of said fluid sample at the fluid sampling interface, wherein the controller comprises a sensor input connected to the sensor to receive a sensor signal from the sensor,
   wherein the controller is configured to adjust a wavelength axis of a measurement based upon a comparison utilizing the wavelength reference material for the entire spectrum collected over a wavelength range of interest.

2. The apparatus of claim 1, wherein the wavelength axis is adjusted by the controller by applying a regression fit over the entire wavelength range of interest whereby both shift and scale operations are performed.

3. The apparatus of claim 1, further comprising a second sensor positioned in a second optical path from the near infrared electromagnetic radiation source, and wherein the controller further comprises a second sensor input connected to the second sensor to receive a second sensor signal from the second sensor.

4. The apparatus of claim 1, wherein said near infrared electromagnetic radiation source is selected from the group consisting of a tungsten-halogen bulb assembly, a near-infrared light emitting diode, a near-infrared superluminescent diode, and a near-infrared tunable laser.

5. The apparatus of claim 1, wherein said optical wavelength selector is an Acousto Optic Tunable Filter (AOTF) tuned for near-infrared operation.

6. The apparatus of claim 1, wherein said optical wavelength selector is selected from the group consisting of a planar reflection diffraction grating, a non-planar reflection diffraction grating, and a transmission diffraction grating.

7. The apparatus of claim 1, wherein said wavelength reference material comprises a polymer selected from the group consisting of polycarbonate, polyimide film, polymethylpentene, polyether ether ketone (PEEK), and nylon.

8. The apparatus of claim 7, wherein said wavelength reference material consists essentially of a single polymer.

9. The apparatus of claim 1, wherein said fluid sampling interface comprises a cartridge, said cartridge comprising a housing, a fluid flow cell attached to the housing and positioned in the optical path, and a receiver assembly comprising at least two optical elements.

10. The apparatus of claim 9, wherein said fluid sampling interface further comprising surfaces to compress said fluid flow cell to form a defined optical path length through the fluid flow cell along the optical path.

11. The apparatus of claim 1, wherein said fluid sampling interface comprises a fiber optically coupled interface and one or more optical fibers optically connecting the optical interface to the near infrared electromagnetic radiation source and the sensor.

12. The apparatus of claim 1, wherein said fluid sampling interface comprises two or more fiber optically coupled interfaces, one or more optical fibers each connected to one of the two or more optical interfaces, and a fiber optic switch connected to each of the one or more optical fibers to selectively connect one of the two or more fiber optically coupled interfaces with the near infrared electromagnetic radiation source or the sensor.

13. The apparatus of claim 1, wherein the controller is connected to a fluid process controller to control a parameter of a fluid process based upon input to the controller from the sensor.

14. The apparatus of claim 13, wherein said parameter of a fluid process is selected from the group consisting of agitation rate, dissolved oxygen, pH, temperature, and foaming within a vessel.

15. The apparatus of claim 1, wherein the controller is connected to a pump and is configured to compare a measured quantity to a target quantity and generate a pump control output to the pump to minimize a difference between said measured quantity and said target quantity by pumping a controlled quantity of a substance into a vessel connected to the pump.

16. The apparatus of claim 1, wherein said controller is further configured to measure one or more quantities and supply at least one external output based upon said quantities to an external instrument.

17. The apparatus of claim 1, further comprising a second fluid interface positioned in a second optical path.

18. The apparatus of claim 1, wherein said sensor comprises a plurality of light sensing elements.

19. A method of determining the quantity of one or more substances in a fluid sample, said method comprising the steps of:
   a. generating a beam of near-infrared electromagnetic radiation;
   b. transmitting at least a portion of said near-infrared electromagnetic radiation through a polymer optical element for wavelength reference, said polymer optical element being at least partially transparent in at least a portion of the near-infrared spectral range, said polymer further comprising an absorption characteristic that differs in magnitude between at least two wavelengths, and adjusting a wavelength axis of a measurement based upon a fit of a transmission spectrum of the wavelength reference material over an entire wavelength range of interest;

c. irradiating a fluid sample within a sampling interface with said near-infrared electromagnetic radiation;

d. sensing near-infrared electromagnetic radiation having interacted with said fluid sample with a sensor; and e. determining a quantity of a substance within said fluid sample.

20. The method of claim 19, wherein said electromagnetic radiation is transmitted through said fluid sample and the measured intensity as a function of wavelength forms a transmission optical spectrum.

21. The method of claim 19, wherein said near-infrared electromagnetic radiation transmitted through said fluid sample comprises wavenumbers between 3300 $cm^{-1}$ and 5600 $cm^{-1}$.

22. The method of claim 19, further comprising the step of sensing a portion of said near infrared electromagnetic radiation not having interacted with said fluid sample with a second sensor as a reference.

23. The method of claim 19, further comprising the steps of detecting air bubbles entrapped in the fluid sample and rejecting measurements contaminated by said air bubbles.

24. The method of claim 19, wherein said beam of near-infrared electromagnetic radiation is generated by a broadband optical emitter.

25. The method of claim 19, wherein said beam of near-infrared electromagnetic radiation is generated by a tunable optical emitter.

26. The method of claim 25, wherein said beam of near-infrared electromagnetic radiation is generated by a near-infrared tunable laser diode (TLD).

27. The method of claim 19, further comprising the step of directing said beam of broadband optical radiation into a wavelength selector.

28. The method of claim 27, wherein said wavelength selector is selected from the group consisting of an Acousto Optic Tunable Filter (AOTF), a planar reflection diffraction grating, a non-planar reflection diffraction grating, and a transmission diffraction grating.

29. The method of claim 19, wherein said fluid sample is not homogeneous.

30. The method of claim 19, wherein said fluid sample is aqueous.

31. The method of claim 19, wherein a transmission distance through the fluid sample is between 0.2 mm and 5 mm.

32. The method of claim 19, wherein the substance within the fluid and for which a quantity is detected is selected from the group consisting of alcohols, sugars, lipids, organic acids, amino acids, fatty acids, and proteins.

33. The method of claim 19, wherein the quantity measured is one or more of cell density, cell viability, or turbidity.

34. The method of claim 19, wherein the quantity of the substance is measured continuously to monitor a fluid process.

35. The method of claim 19, wherein the wavelength axis of a measurement is adjusted multiple times during a fluid process.

36. The method of claim 19, wherein said quantity of the substance is measured in real-time to monitor a fluid process.

37. The method of claim 19, wherein a frequency at which the quantity of the substance is measured is greater than 1 per minute.

38. The method of claim 19, wherein said fluid sample is circulated from the process through a fluid conduit.

39. The method of claim 19, wherein the step of determining a quantity of a substance in the fluid sample is performed by means of one or more optical fibers.

40. The method of claim 19, wherein said polymer optical element for wavelength reference is intermittently positioned at least partially within a path of said electromagnetic radiation.

41. The method of claim 19, wherein said fluid sample is from a continuous process.

42. The method of claim 19, further comprising an additional analysis selected from the list consisting of electrochemical, fluorescence, UV-Vis absorption, and Raman analysis.

43. A method of controlling a fluid process, said method comprising the steps of:

a. generating a beam of near infrared electromagnetic radiation;

b. transmitting at least a portion of said near infrared electromagnetic radiation through a polymer element for wavelength reference, said polymer optical element being at least partially transparent in at least a portion of the near infrared spectral range, said polymer further comprising an absorption characteristic that differs in magnitude between at least two wavelengths, and adjusting a wavelength axis of a measurement based upon a fit of a transmission spectrum of the wavelength reference material over an entire wavelength range of interest;

c. irradiating a fluid sample within a sampling interface with near-infrared electromagnetic radiation;

d. sensing near-infrared electromagnetic radiation having interacted with said fluid sample with a sensor;

e. determining based on an output from the sensor and the optical wavelength selector one or more quantities of components of or materials suspended within said fluid sample; and f. using said determined one or more quantities to adjust one or more parameters or quantities of a substance in said fluid process.

44. The method of claim 43, further comprising the step of controlling the quantity of at least one substance in the fluid process.

45. The method of claim 43, further comprising the step of controlling one or more parameters in the fluid process.

46. The method of claim 43, wherein said one or more parameters are selected from the group consisting of agitation rate, dissolved oxygen, pH, and foaming within the vessel.

47. The method of claim 43, wherein said controlling step controls a target concentration or concentration profile based upon at least one quantity determined based on the output from the sensor.

48. The method of claim 43, wherein said controlling step controls a target concentration or concentration profile based upon at least one substance consumption rate determined based on the output from the sensor.

49. The method of claim 43, wherein said controlling step controls a target concentration or concentration profile based upon at least one cell growth rate determined based on the output from the sensor.

50. The method of claim 43, further comprising process adjustments based on one or more additional analyses selected from the list consisting of electrochemical, fluorescence, UV-Vis absorption, and Raman analysis.

* * * * *